US008048425B2

(12) United States Patent
Raines et al.

(10) Patent No.: US 8,048,425 B2
(45) Date of Patent: Nov. 1, 2011

(54) CYTOTOXIC RIBONUCLEASE VARIANTS

(75) Inventors: Ronald T. Raines, Madison, WI (US); George N. Phillips, Jr., Madison, WI (US); R. Jeremy Johnson, Middleton, WI (US); Jason G. McCoy, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/497,038

(22) Filed: Jul. 2, 2009

(65) Prior Publication Data

US 2009/0311784 A1 Dec. 17, 2009

Related U.S. Application Data

(63) Continuation of application No. 11/454,418, filed on Jun. 16, 2006, now Pat. No. 7,655,757.

(60) Provisional application No. 60/691,311, filed on Jun. 16, 2005.

(51) Int. Cl.
*A61K 39/385* (2006.01)

(52) U.S. Cl. .................................................... 424/193.1

(58) Field of Classification Search ........................ None
See application file for complete search history.

(56) References Cited

U.S. PATENT DOCUMENTS

| | | | |
|---|---|---|---|
| 5,840,296 | A | 11/1998 | Raines et al. |
| 6,280,991 | B1 | 8/2001 | Raines et al. |
| 7,416,875 | B2 | 8/2008 | Raines et al. |
| 7,655,757 | B2 | 2/2010 | Raines et al. |
| 2005/0261232 | A1 | 11/2005 | Strong et al. |
| 2006/0292137 | A1 | 12/2006 | Raines et al. |
| 2009/0311784 | A1 | 12/2009 | Raines et al. |

FOREIGN PATENT DOCUMENTS

| | | | |
|---|---|---|---|
| AU | 778024 | | 3/2005 |
| AU | 2002301972 | B2 | 3/2006 |
| CA | 2306442 | | 4/2010 |
| EP | 1896579 | A2 | 3/2008 |
| EP | 1023447 | | 8/2008 |
| EP | 1910541 | B1 | 10/2010 |
| IL | 143036 | | 9/2009 |
| JP | 200817144 | | 5/2008 |
| JP | 2008517102 | A1 | 5/2008 |
| WO | 9919494 | A1 | 4/1994 |
| WO | 0031242 | A2 | 3/2000 |
| WO | 0040608 | | 7/2000 |
| WO | 2006138458 | A1 | 12/2006 |

OTHER PUBLICATIONS

Burgess et al. (J. Cell Biol. 111:2129-2138, 1990).*
Lazar et al. ( Mol. Cell Biol. 8:1247-1252, 1998).*
Newton et al (The Journal of Neuroscience, 1994, 14(2): 538-544).*
Boix, E., et al, "Role of the N Terminus in RNase A Homologues: Differences in Catalytic Activity, Ribonuclease Inhibitor Interaction and Cytotoxicity," J. Mol. Biol. 257:992-1007 (1996).
Bosch, M. et al., "A Nuclear Localization Sequence Endows Human Pancreatic Ribonuclease With Cytotoxic Activity," Biochemistry 43:2167-2177 (2004).
Gaur, D., et al., "Interaction of Human Pancreatic Ribonuclease with Human Ribonuclease Inhibitor," The Journal of Biological Chemistry 276:24978-24984(2001).
Kobe, B., et al., "A structural basis of the interactions between leucine-rich repeats and protein ligands," Nature 374-:183-186 (1995).
Kobe, G. et al., "Mechanism of Ribonuclease Inhibition by Ribonuclease Inhibitor Protein Based on the crystal Structure of its Complex with Ribonuclease A." J. Mol. Biol. 264:1028-1043 (1996).
Kumar, K. et al., "Selective abolition of pancreatic RNase binding to its inhibitor protein," PNAS 101:53-58 (2004).
Lee, J.E., et al., "Cytotoxicity of Bovine Seminal Ribonuclease: Monomer versus Dimer," Biochemistry 44:15760-15767 (2005).
Leland, P.A.,et al., "Ribonuclease A variants with potent cytotoxic activity," Proc. Natl. Acad. Sci. USA 95:10407-10412 (1998).
Leland, P.A. et al., Endowing Human Pancreatic Ribonuclease with Toxicity for Cancer Cells, The Journal of Biological Chemistry 276:43095-43102 (2001).
Mitchell, J.C., et al., "Rapid atomic density methods for molecular shape characterization," Journal of Molecular Graphics and Modeling 19:325-330 (2001).
Pous, J., et al., "Three-dimensional Structure of a Human Pancreatic Ribonuclease Varient, a Step Forward in the Design of Cytotoxic Ribonucleases," J. Mol. Biol. 303:49-59 (2000).
Pous, J., et al., "Three-dimensional Structure of Human RNase 1 delta N7 at 1.9 a resolution," Acta Cryst. D57:498-505 (2001).
Rajamani, D., et al., "Anchor residues in protein-protein interactions," PNAS 101:11287-11292 (2004).
Rutkoski, T.J., et al., "Disruption of Shape-Complementarity Markers to Create Cytotoxic Varients of Ribonuclease A," J. Mol. Biol. 354:41-54 (2005).
Shaul, Y., et al., "Exploring the Charge Space of Protein-Protien Association: A Proteomic Study," Proteins: Structure, Function, and Bioinformatics 60:331-352 (2005).
Gura (Science,1997, 278:1041-1042).
Murphy, B.S., et al., "Sensitivity of monomeric and dimeric forms of bovine seminal ribonuclease to human placental ribonuclease inhibitor," Biochem, J. 281:343-348 (1992).
Rutkoski, T.J., et al., "Disruption of Shape-Complementarity Markers to Create Cytotoxic Variants of Ribonuclease A." J. Mol. Biol. 354:41-54 (2005).
Quintessence/Biosciences webpage on Evade TM Ribonucleases, (2009).
Burgess, et al., (J. Cell Biol. 111:2129-2138, 1990).
Lazar, et al., (Mol. Cell Biol. 8:1247-1252, 1998).
Ontjes, et al., (PNAS, Oct. 1969, 64(2): 428-35).
International Search Report dated Nov. 13, 2006 (International Patent Application No. PCT/US2006/023298; filed on Jun. 16, 2006).
Written Opinion dated Dec. 16, 2007 (International Patent Application No. PCT/US2006/023298; filed on Jun. 16, 2006).

(Continued)

*Primary Examiner* — Sean Aeder
(74) *Attorney, Agent, or Firm* — Quarles & Brady LLP; Sara D. Vinarov

(57) ABSTRACT

This invention relates to cytotoxic variants of human ribonuclease 1 (RNase 1) identified through analysis of the interaction between RNase 1 and the human ribonuclease inhibitor (hRI) as defined by the three dimensional (3-D) atomic structure of the RNase1 hRI complex. Also disclosed is the 3-D structure of the hRI•RNase 1 complex and methods for designing the RNase 1 variants.

20 Claims, 6 Drawing Sheets

OTHER PUBLICATIONS

International Preliminary Report on Patentability dated Dec. 17, 2007 (International Patent Application No. PCT/US2006/023298; filed on Jun. 16, 2006).
International Search Report dated Aug. 2, 2007 (International Patent Application No. PCT/US2006/023485; filed on Jun. 16, 2006).
Written Opinion dated Dec. 16, 2007 (International Patent Application No. PCT/US2006/023485; filed on Jun. 16, 2006).
International Preliminary Report on Patentability dated Dec. 17, 2007 (International Patent Application No. PCT/US2006/023485; filed on Jun. 16, 2006).
International Search Report dated Nov. 23, 2000 (International Patent Application No. PCT/US19927670; filed on Nov. 22, 1999).
Notice of Allowance dated Apr. 17, 2008 (U.S. Appl. No. 11/454,379, filed Jun. 16, 2006).
Non-Final Rejection dated Aug. 9, 2007 (U.S. Appl. No. 11/454,379, filed Jun. 16, 2006).
Non-Final Rejection dated May 16, 2006 (U.S. Appl. No. 11/454,418, filed Jun. 16, 2006).
Non-Final Rejection dated Sep. 5, 2007 (U.S. Appl. No. 11/454,418, filed Jun. 16, 2006).
Non-Final Rejection dated Mar. 9, 2007 (U.S. Appl. No. 11/454,418, filed Jun. 16, 2006).
Final Rejection dated Oct. 31, 2008 (U.S. Appl. No. 11/454,418, filed Jun. 16, 2006).
Advisory Action dated Jan. 13, 2009 (U.S. Appl. No. 11/454,418, filed Jun. 16, 2006).
Murphy et al., "Sensitivity of monomeric and dimeric forms of bovine seminal ribonuclease to human placental ribonuclease inhibitor", Biochem. J. Mol. Biol. 354:41-54 (2005).
Quintessence/Biosciences webpages on Evade TM Ribonucleases, May 9, 2011.
Communication under Rule 71 (3) EPC (European Patent Application No. 98951054.0-2401, filed Oct. 13, 1998).
Examination Report dated May 14, 2003 (European Patent Application No. 98951054.0-2401, filed Oct. 13, 1998).
Examination Report dated Mar. 9, 2004 (European Patent Application No. 98951054.0-2401, filed Oct. 13, 1998).
Examination Report dated Apr. 27, 2005 (European Patent Application No. 98951054.0-2401, filed Oct. 13, 1998).
Notice of Allowance dated Sep. 29, 2009 (Canadian Patent Application No. 2306442, filed Oct. 13, 1998).
Office Action dated Dec. 4, 2007 (Canadian Patent Application No. 2306442, filed Oct. 13, 1998).
Office Action dated Oct. 20, 2006 (Canadian Patent Application No. 2306442, filed Oct. 13, 1998).
Examiner's Report dated Nov. 17, 2004 (Australian Patent Application No. 2002301972, filed Nov. 13, 2006).
Examiner's Report dated Aug. 10, 2005 (Australian Patent Application No. 2002301972, filed Nov. 13, 2006).
Notice of Acceptance dated Nov. 22, 2005 (Australian Patent Application No. 2002301972, filed Nov. 13, 2006).
Kim et al., Structural Basis for the Biological Activities of Bovine Seminal Ribonuclease, J. Biol. Chem. 270, No. 18: 10 525-1 0530, 1995.
Murthy et al., Sensitivity of monomeric and dimeric forms of bovine seminal ribonuclease to human placental ribonuclease inhibitor (Biochem. J., 1992, 281:343-348).
Schein, From Housekeeper to Microsurgeon: The Diagnostic and Therapeutic Potential of Ribonucleases, Nature Biotechnology 15:529-536, 1997.
Non-Final Rejection dated Feb. 9, 2011 (U.S. Appl No. 12/497,038, filed Jul. 2, 2009).
Requirement for Restriction/Election dated Oct. 5, 2010 (U.S. Appl No. 12/497,038, filed Jul. 2, 2009).
Communication under Rule 71(3) EPC dated May 4, 2010 (Appl. No. 06784926.5, filed Jun. 16, 2006).
Examination Report dated Aug. 19, 2009 (EP Patent Application No. 06784995.0-2401, filed Jun. 16, 2006).
Examination Report dated Nov. 2, 2010 (EP Patent Application No. 06784995.0-2401, filed Jun. 16, 2006).
Examination Report dated Nov. 21, 2008 (Application No. 06784926.5, filed Jun. 16, 2006).
Examination Report dated Aug. 25, 2008 (European Patent Application No. 99962862821.7, filed Nov. 22, 1999).
Examination Report dated Jan. 20, 2005 (European Patent Application No. 99962862821.7, filed Nov. 22, 1999).
Notice of Allowance dated Jan. 10, 2004 (Australian Patent Application No. 19184/00, filed Mar. 3, 2005).
Examiner's Report dated Jan. 17, 2003 (Australian Patent Application No. 19184/00, filed Mar. 3, 2005).
Office Action dated Nov. 24, 2009 (Canadian Patent Application No. 2,351,735, filed Nov. 22, 2009).
Office Action dated Nov. 28,2007 (Canadian Patent Application No. 2,351,735, filed Nov. 22,2009).
Messmore, et al., Ribonuclease A: Revealing structure—function relationships with semi synthesis, Journal of the American Chemical Society, vol. 117, No. 31, (Aug. 9, 1995).
Reddy, et ai Folate-mediated targeting of the therapeutic and imaging agents to cancer, Critical Reviews in Therapeutic Drug Carrier Systems, vol. 15, No. 6, 1998, pp. 587-627.
Kim, et al., Mechanism of ribonuclease cytotoxicity, the Journal of of Biological Chemistry, vol. 270, No. 52 (Dec. 29, 1995) pp. 31097-311102.
Office Action dated Aug. 6, 2009 (Japanese Patent Application No. 2000-584053, filed Nov. 22, 1999).
Final Rejection (Japanese Patent Application No. 2000-584053, filed Nov. 22, 1999).
International Search Report dated Feb. 16, 2009 (International Patent Application No. PCT/US1998/021545, filed Oct. 13, 1998).
Sendak, et al., Kinetic and thermodynamic studies of the folding/unfolding of a typrtophan-containing mutant of rubinuclease A, Biochemistry, col. 35, 1996, pp. 12978-12992.
Schultz et al., Structure stability of the P93G variant of ribonuclease A, Protein Science, vol. 7, Jul. 1998, pp. 1620-1625.
Alfacell Corporation, Reports and Press Releases from Oct. 1994-Nov. 1996.
Leu, Y-J., et al., "Residues Involved in the catalysis, Base Specificity, and Cytotoxicity of Ribonuclease" The Journal of Biological Chemistry 278:7300-7309 (2003).
Branden et al., Introduction to Protein Structure, Garland Publishing Inc., New York, p. 247, 1991.
Witkowski et al., Biochemistry 38:11643-11650, 1999.
Seffernick et af., J. Bacteriol. 183(8):2405-2410,2001.

* cited by examiner

CYTOTOXIC RIBONUCLEASE VARIANTS

CROSS-REFERENCE TO RELATED APPLICATIONS

This application is a continuation of U.S. Nonprovisional application Ser. No. 11/454,418 filed Jun. 16, 2006 now U.S. Pat. No. 7,655,757, which claims priority to U.S. Provisional Application No. 60/691,311 filed Jun. 16, 2005. Each of these applications is incorporated by reference here in its entirety.

STATEMENT REGARDING FEDERALLY SPONSORED RESEARCH AND DEVELOPMENT

This invention was made with United States government support awarded by the following agency: NIH CA073808 and GM 064598. The United States government has certain rights in this invention.

BACKGROUND OF THE INVENTION

Ribonucleases are enzymes that catalyze the degradation of RNA. A well studied ribonuclease is bovine pancreatic ribonuclease A (RNase A), the putative biological function of which is to break down the large amount of RNA that accumulates in the ruminant gut. The RNase A superfamily is a group of RNase enzymes classified as similar to RNase A which possess a number of interesting biological properties including antiproliferative, cytotoxic, embryotoxic, aspermatogenic, and antitumoral activities. One member of this family is a homolog of RNase A, originally isolated from oocytes and early embryos of the Northern leopard frog *Rana pipiens.*

The frog (*Rana pipiens*) ribonuclease, when placed in a human cell, is not strongly-inhibited by RI and its RNase activity destroys cellular RNA and kills the target cell. The anti-tumor properties, both in vitro and in vivo, of the frog ribonuclease are described and claimed in U.S. Pat. No. 5,559,212. This ribonuclease molecule is now known as Onconase® (ONC). The property of degrading RNA is essential to the cytotoxicity of ONC. ONC is currently being evaluated as a cancer therapeutic in clinical trials.

A significant limitation on the suitability of ONC as a chemotherapeutic is dose-limiting renal toxicity. ONC is retained in the kidney at concentrations much greater than mammalian members of the RNase superfamily. There may also be allergenic issues with ONC, since mice produce antibodies against ONC but not against RNase A, with which ONC shares about 30% of its amino acids. This suggests that other members of the RNase family may also be suitable candidates for evaluation as clinical therapeutics if they can be imbued with the cytotoxic properties similar to ONC.

In mammals, levels of RNase activity are controlled by a ribonuclease inhibitor (RI), which is a 50-kDa protein found in the cytosol of all mammalian cells. RI is a member of a leucine rich family of proteins and is composed of 15 alternating repeats arranged symmetrically in a horseshoe shaped molecule. RI has a large number of cysteine residues (32 in human RI) which means that it can only keep its shape and function in a reducing environment like the cytosol. RI acts to bind to members of the RNase superfamily, one RI to one molecule of RNase, and when so bound, RI completely inhibits the catalytic activity of the ribonuclease by steric blockage of the active site of the enzyme. The binding of RI to RNase is a very tight one, having a very high binding affinity.

Some RNase superfamily members, notably ONC and bovine seminal ribonuclease, possess the native ability to evade RI. The trait of evasion of RI is primarily responsible for the cytotoxicity of ONC and bovine seminal ribonuclease. It has also been found that RNase superfamily members, which are not natively cytotoxic, can be made cytotoxic by modifying their amino acid constituents, so as to inhibit binding to RI.

Using the three dimensional structure of the porcine RI (pRI)-RNase A complex, RNase A was engineered to be more toxic to human leukemic cells in vitro than ONC. Disruption of the RI•RNase A interface was accomplished by designing RNase A variants with amino acid substitutions that disrupted complementarity regions at the pRI•RNase A interface. These amino acid substitutions targeted short range pRI•RNase A interactions by incorporating sterically disruptive amino acids or removing hydrogen bonds. This method is described in U.S. Pat. No. 5,840,296, incorporated by reference herein in its entirety. Analogous complementarity regions were applied to bovine seminal ribonuclease (BS-RNase, 87% sequence similarity) a close homologue of RNase A. However, a BS-RNase variant with mutations at the same complementarity regions was less cytotoxic than ONC or the most cytotoxic RNase A variant (D38R/R39D/N67R/G88R RNase A). This strategy did not result in the level of cytotoxicity predicted for BS-RNase.

Furthermore, most of the work done so far in the creation of RNase A variants has been done with bovine RNase A. However, the sequence and structure of bovine RNase A (SEQ ID NO:1, GenBank Accession No. AAA72757) differs from human pancreatic ribonuclease 1 (RNase 1) (SEQ ID NO: 2, GenBank Accession No. CAG29314, incorporated by reference herein in its entirety), RNase A and its homolog, RNase 1 share about 70% sequence identity of their amino acid sequences. While the bovine protein may prove out to be acceptable for use in human therapy, a conservative approach might be to utilize a variant of a human ribonuclease, on the theory that use of a human protein might minimize cross-species antigenic problems. Accordingly, it is desirable to design variants of human ribonucleases that may be more cytotoxic and effective for therapeutic, diagnostic or research use.

BRIEF SUMMARY OF THE INVENTION

The present invention is summarized as variants of human ribonuclease 1 (RNase 1) identified through analysis of the interaction between RNase 1 and the human ribonuclease inhibitor (hRI), as defined by the three dimensional (3-D) atomic structure of the hRI•RNase 1 complex.

In one aspect, the present invention defines an RNase 1 that has improved cytotoxic properties compared to all previously disclosed engineered ribonucleases.

In another aspect, the invention provides a variant RNase 1 having a modified amino acid sequence, wherein the variant RNase 1 retains its ribonucleolytic activity, and wherein the variant RNase 1 has a lower binding affinity for RI than that of the native RNase 1 and retains native ribonucleolytic activity.

In this aspect, the human RNase 1 variant includes at least two amino acid changes from its native sequence, the changes causing evasion of human hRI by RNase 1 through electrostatic repulsion, the first change being an amino acid substitution in the region of amino acid residues 85 to 94 of RNase 1, and the second change being an alteration, substitution or amino acid swap at a location selected from the group consisting of amino acid residues 4, 7, 11, 31, 32, 38, 39, 41, 42, 66, 67, 71, 111 and 118 of RNase 1, wherein the variant RNase 1 exhibits enhanced cytotoxic activity relative to the native RNase 1.

In a related aspect, the human RNase 1 variant includes at least two amino acid changes from its native sequence, the changes causing evasion of human hRI by RNase 1 through electrostatic repulsion, the first change being an amino acid substitution at amino acid residue 88 or 91 of RNase 1, and the second change being an alteration, substitution or amino acid swap at a location selected from the group consisting of amino acid residues 4, 7, 11, 31, 32, 38, 39, 41, 42, 66, 67, 71, 111 and 118 of RNase 1, wherein the variant RNase 1 exhibits enhanced cytotoxic activity relative to the native RNase 1.

The present invention further provides variants of RNase 1 with amino acids modified from the native sequence. Exemplary variants are provided in Table 5 herein below. Additional variants that have the desired function are also within the scope of the invention.

In a preferred aspect, the RNase 1 variant is defined by R39D/N67D/N88A/G89D/R91D and has at least $10^7$-fold lower affinity and 2700-fold lower association rate for hRI than wild-type (native) RNase 1.

In another aspect, the present invention provides a method for modifying the amino acid sequence of a native RNase 1 to produce a novel, cytotoxic RNase 1.

The present invention is a method for modifying the amino acid sequence of RNase 1 to produce a variant RNase 1, which retains its ribonucleolytic activity, and wherein the variant RNase 1 has a binding affinity for RI that is lower than that of the native RNase 1 and retains native ribonucleolytic activity.

The present invention is also a method for inhibiting the proliferation of cancer cells, comprising delivering to the cells an effective amount of a modified RNase 1, wherein the variant RNase 1 has a binding affinity for RI that is lower than that of the native RNase 1 and retains native ribonucleolytic activity.

In another aspect, the invention provides a method of engineering cytotoxic RNase 1 variants by identifying electrostatic anchor residues in the three dimensional structure of the hRI•RNase 1 complex; and modifying the anchor residues identified in RNase 1 to inhibit binding to hRI through electrostatic repulsion, wherein the variants retain native ribonucleolytic activity, have a lower binding affinity for hRI than that of the native RNase 1, and exhibit enhanced cytotoxic activity relative to the native RNase 1.

In another aspect, the invention provides a crystal of a hRI•hRNase 1 complex as defined by Protein Data Bank identification No. 1Z7X.

Also, disclosed is a method of using the three-dimensional structure coordinates of the hRI*RNase 1 complex to design RNase 1 variants that retain native ribonucleolytic activity, have a lower binding affinity for hRI than that of the native RNase 1, and exhibit enhanced cytotoxic activity relative to the native RNase 1.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other objects, advantages and features of the present invention will become apparent from the following specification taken in conjunction with the accompanying drawings.

DETAILED DESCRIPTION OF THE INVENTION

Figure 1A:
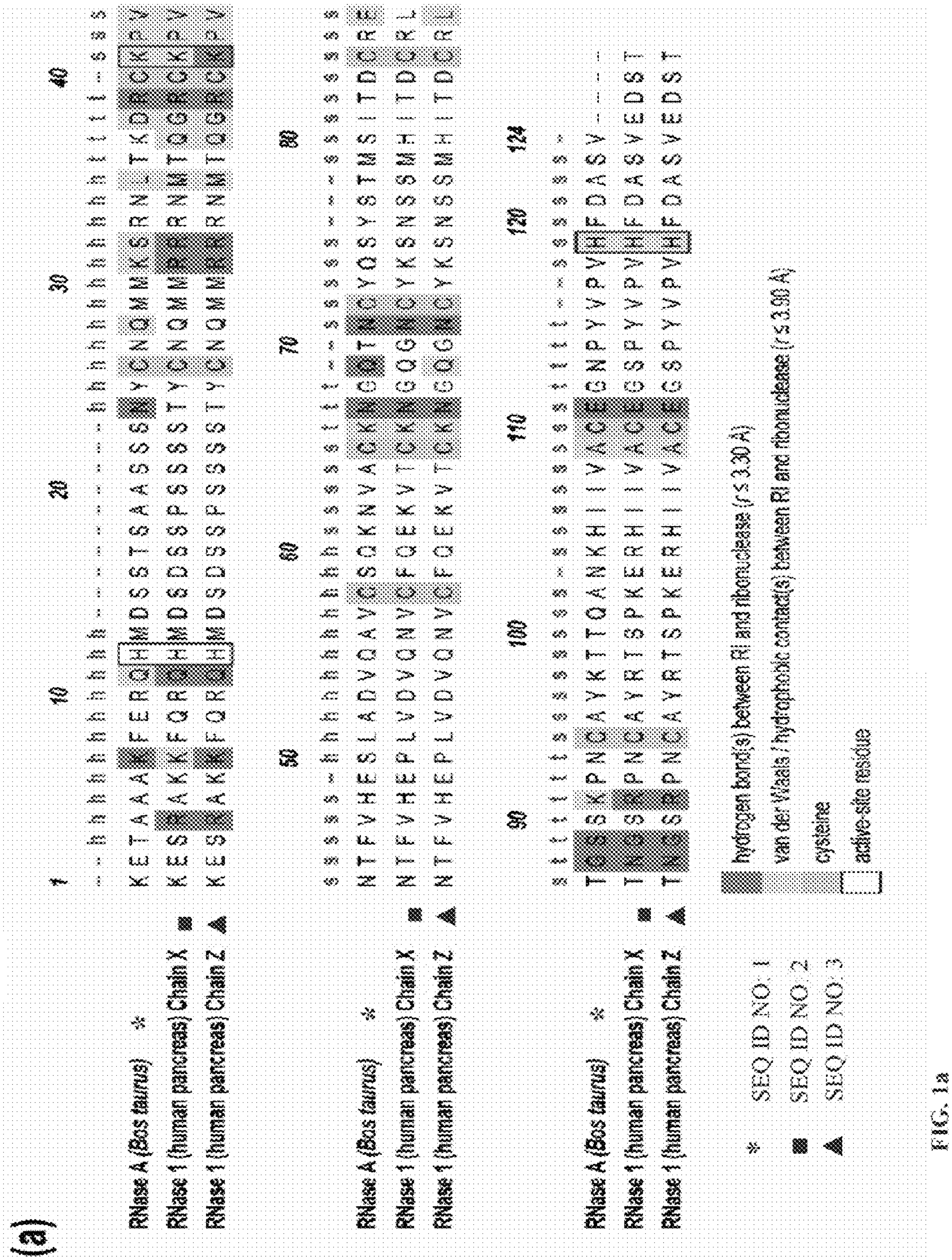
FIGS. 1A-B show RI contact residues of RNase 1 and RNase A. (A) Amino acid sequence alignment of RNase A and RNase 1. (B) Three-dimensional structure of RNase 1 chain Z from PDB Identification No. 1Z7X.

The present invention relates to novel human ribonuclease 1 variants engineered to exhibit an increased level of cytotoxic activity relative to the native RNase 1. This was made possible for the first lime through the determination of the three dimensional (3-D) atomic crystal structure of the human ribonuclease inhibitor (hRI, SEQ ID NO: 4) molecule bound to the human ribonuclease 1 (RNase 1) molecule. The structure of the hRI•RNase 1 complex has a 1.95 Å resolution and the atomic coordinates were deposited in the publicly available sequence database, Protein Data Bank (PDB), accession No. 1Z7X.

Using the 3-D structure of the hRI•RNase 1 complex, the interaction between hRI and RNase 1 in complex was characterized and used to determine the energetic contribution of specific RNase 1 residues to RI binding. The interaction between long range electrostatics and the rate of association was analyzed to identify electrostatic contributions of anchor residues in the hRI•RNase 1 complex. These residues were rationally modified to (1) evade hRI by inhibiting the binding of the anchor residues through electrostatic repulsion and (2) increase cytotoxic activity relative to the native RNase 1. Using the logic described here, it is believed that we were able to overcome a major obstacle to the development of chemotherapeutics based on human ribonucleases.

In a broad embodiment, the invention provides an engineered ribonuclease variant of RNase 1 having at least two amino acid changes from its native sequence, the changes causing evasion of hRI by RNase 1 through electrostatic repulsion, the first change being an amino acid substitution in the region of amino acid residues 85 to 94 of RNase 1, and the second change being an alteration, substitution or amino acid swap at a location selected from the group consisting of amino acid residues 4, 7, 11, 31, 32, 38, 39, 41, 42, 66, 67, 71, 111 and 118 of RNase 1, the variant RNase 1 having cytotoxic activity relative to the native RNase 1. Such variants are designated herein by the notation XNNY, where Y is the substituted amino acid residue for the residue X normally found at location NN (e.g., R4C).

As used herein, the terms, "native", "wild-type", "unmodified" are synonymous with each other. They refer to a gene product that has the characteristics of that gene product when isolated from a naturally occurring source. A wild-type gene is that which is most frequently observed in a population and is thus arbitrarily designed the "normal" or "wild-type" form of the gene.

In contrast, the terms "variant", "modified", or "mutant" refer to a gene product that displays modifications in sequence and or functional properties (i.e., altered characteristics) when compared to the wild-type gene product. The invention provides for variants of RNase 1 Exemplary variants are described in Table 5.

In one embodiment, the invention provides a RNase 1 variant having an amino acid change at residues 4, 38, 39, 67, 88, 89, 91 an 118 causing evasion of human Ribonuclease Inhibitor (hRI) by RNase 1 through electrostatic repulsion relative to the native sequence, SEQ ID NO:2, wherein the variant RNase 1 retains its native ribonucleolytic activity, has a lower binding affinity for RI than that of the native ribonuclease, and exhibits enhanced cytotoxic activity relative to the native RNase 1.

Based on this embodiment, we synthesized R4C/G38R/R39G/N67R/N88L/G89R/R91G/V118C RNase 1, which is an instructive variant of human pancreatic ribonuclease. This enzyme has changes to eight residues, inspired by the atomic structure of the hRI•RNase 1 complex as presented here. Residues Gly38, Arg39, Asn67, Asn88, Gly89, and Arg91 are all near the interface of the hRI•RNase 1 complex. The replacement of these residues in the variant is designed to interfere with the interface. Arg4 and Val118 are also near the hRI•RNase 1 interface. Their replacement with cysteine residues is designed to interfere with this interface as well as allowing for the formation of a new disulfide bond between Cys4 and Cys118, which is likely to confer extra conformational stability to the enzyme. This RNase 1 variant (1) retains nearly all of the enzymatic activity of the native RNase 1, (2) evades hRI, and (3) exhibits significant cytotoxic activity.

In a preferred embodiment, the invention provides RNase 1 variants having an amino acid change at residues 39, 67, 88, 89 and 91 relative to the native sequence, SEQ ID NO:2, wherein the variants retain native ribonucleolytic activity, have a lower binding affinity for RI than that of the native RNase 1, and exhibit enhanced cytotoxic activity relative to the native RNase 1.

These RNase 1 variants were designed by applying the relationship between long range electrostatics and the rate of association. A preferred RNase 1 variant is defined by R39D/N67D/N88A/G89D/R91D and has $10^7$-fold lower affinity and 2700-fold lower association rate for hRI than wild-type RNase 1. The 2700-fold lower association rate was 25-fold gain of electrostatic repulsion by aspartate substitution in RNase 1 and 110-fold loss of electrostatic attraction at positions 39 and 91 in RNase 1.

It is noted that in the hRI•RNase 1 complex, electrostatic attraction of key charged residues like Arg39 and Arg91 helps hRI recognize RNase 1 more than sterically constrained residues like Asn67 do. RI uses its horseshoe shaped structure to allow long-range electrostatic interactions by key solvent-exposed charged residues (especially Arg39 and Arg91) to determine its tight interaction with RNase 1.

Other novel variants of RNase 1 are also described herein which retain native ribonucleolytic activity, have a lower binding affinity for RI than that of the native RNase 1, and exhibit enhanced cytotoxic activity relative to the native RNase 1. These include RNase 1 variants, which have an amino acid change relative to the native sequence, SEQ ID NO:2 at (1) residues 39, 67, 89 and 91, preferably, R39D/N67A/G89D/R91D; (2) residues 39, 67, 88 and 91, preferably R39D/N67D/N88A/R91D; (3) residues 39, 67, 88 and 89, preferably R39D/N67D/N88A/G89D; (4) residues 39, 88, 89 and 91, preferably R39D/N88A/G89D/R91D; (5) residues 38, 39, 67, and 88, preferably G38R/R39G/N67R/N88R; and residues 67, 88, 89 and 91, preferably 67D/N88A/G89D/R91D.

In another embodiment, the invention provides method of modifying RNase 1 to make cytotoxic RNase 1 variants by identifying electrostatic anchor residues in the three dimensional structure of the hRI•RNase 1 complex; and modifying the anchor residues identified in RNase 1 to inhibit binding to hRI through electrostatic repulsion, wherein the variants retain native ribonucleolytic activity, have a lower binding affinity for hRI than that of the native RNase 1, and exhibit enhanced cytotoxic activity relative to the native RNase 1. Thus, through exploitation of the electrostatic attraction between hRI and RNase 1 we were able to develop variants of RNase 1 that are capable of eluding the inhibitory binding of RI to overcome a major hurdle in the development of human ribonuclease-based chemotherapeutics.

In another embodiment, the invention provides a method for inhibiting the proliferation of cancer or tumor cells, comprising delivering to the cells an effective amount of a variant RNase 1, wherein the variant RNase 1 exhibits enhanced cytotoxic activity relative to the native RNase 1.

By "enhanced cytotoxicity" it is meant that the modified RNase 1 exhibits greater cytotoxicity than the corresponding unmodified or native (wild-type) RNase 1. In the examples below, cytotoxicity was evaluated using the human erythroleukemia cell line K-562. It is anticipated that the modified ribonuclease of the present invention is cytotoxic against other tumor cells in addition to that which is described herein. Inhibition of cell proliferation is determined by calculating the percentage of viable K-562 cells treated with the modified or unmodified RNase 1, where 100% viability is considered to be the number of viable cells that were treated with a solution of phosphate-buffered saline (PBS).

By "effective amount" is meant that amount of ribonuclease needed to cause a significant reduction in the proliferation of the tumor cells.

Preferably, the modified ribonuclease reduces cell viability by at least about 10%. More preferably, the modified ribonuclease reduces cell viability by at least about 20%. Most preferably, the modified ribonuclease reduces cell viability by about 50%, or even as much as about 75%.

In another embodiment, the invention provides a hRI•RNase 1 complex as defined by the Protein Data Bank identification No. 1Z7X. The 3-D atomic crystal structure of the hRI•RNase 1 complex is described here for the first time. The atomic coordinates for the crystal structure of the hRI•RNase 1 complex are set forth here in Appendix 1. These atomic coordinates were also deposited at the Research Collaborator) for Structural Bioinformatics Protein Data Bank (PDB) and assigned the accession number PDB ID No: 1Z7X. The 3-D structure of the hRI•RNase 1 complex can be used as a tool to rationally design RNase 1 variants that evade hRI and that exhibit enhanced cytotoxic activity relative to the native enzyme.

The research value of the 3-D structure of the hRI•RNase 1 complex is understood to those skilled in the art. It will also be appreciated that the structure obtained from X-ray crystallography is only a static snapshot of the protein-ligand complex. In reality, proteins like RNase 1 are highly flexible macromolecules, changing their conformation on various time scales. Access to potential binding sites may only be available in certain conformations. It is envisioned that techniques, namely Molecular Dynamics, normal Mode or Monte Carlo methods, may be used to capture one or more representative structures for designing other RNase 1 variants.

While this patent specification contains several examples of protein and amino acid sequences, it should be understood that all protein sequences are subject to minor changes and modifications without fundamentally changing the proteins or the concept of the present invention. Conservative changes of amino acids of similar size and polarity are always possible and rarely change the functioning of a protein. The whole RNase 1 is subject to further modifications of sequence, either by minor amino acid addition, deletion of substitution without adversely affecting the activity as a RNase 1. These kinds of changes in amino acid sequence are interpreted to be within the scope of the language used herein.

A conservative amino acid substitution includes one or more amino acid residues within the sequence that can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Such alterations will not be expected to affect apparent molecular weight as determined by polyacrylamide gel electrophoresis, or isoelectric point. Abbreviations of amino acids are known in the art The invention is further clarified by consideration of the following examples, which are intended to be purely exemplary of the method of the present invention.

EXAMPLES

1. Experimental Overview

Design of RNase 1 Variants

In general, it is understood by those skilled in the art that the equilibrium dissociation constant ($K_d$) of a protein complex is governed by the intermolecular factors influencing the rate of association ($k_{on}$) and dissociation ($k_{off}$). The rate of dissociation is influenced by factors that act over short distances, including van der Waals interactions, hydrogen bonds, hydrophobic interactions, and salt bridges. The rate of association, however, depends primarily on diffusion but can be increased through Coulombic electrostatic forces. The majority of long-range electrostatic forces destabilize protein-protein interactions due to a large energetic penalty to desolvate the charged amino acids. However, when speed is a necessity, the rate of association and consequently the affinity of a complex can be increased by optimizing the electrostatic energy.

In designing proteins to have lower affinity for their interacting protein partner, either component of the kinetic rate ($k_{on}$ or $k_{off}$) could be targeted. Previous inhibition studies of the RI•RNase interface have focused on short range intermolecular contacts between RI•RNase, effectively raising the dissociation rate. Detrimentally affecting the affinity of RNase 1, the human homologue of RNase A, using short range interactions has proven more difficult.

To overcome this hurdle, we determined the crystal structure of the hRI•RNase 1 complex at 1.95 Å resolution and employed the structural information to design variants of RNase 1 with micromolar affinity for hRI (GenBank Accession No. P13489). We also investigated with RNase 1 the analogous complementarity residues identified in RNase A and revealed the energetic contribution to RI binding from these RNase 1 residues. Based on the contribution of these charged residues (e.g., Arg39 and Arg91) to the rate of complex association, we define a role for "electrostatic anchor" residues in determining protein-protein interactions. Electrostatic anchor residues determine protein-protein recognition by (1) contributing substantial enhancement to the association rate, and (2) maintaining complex formation through tight hydrogen bonds. Overall, the evasion of RI by RNase 1 requires both steric and electrostatic contributions, but is driven to micromolar affinity by a significant decrease in the association rate constant.

Accordingly, the cytotoxic RNase 1 variants of the present invention were developed by (1) analyzing the molecular recognition patterns of RI in complex with RNase 1 and RNase A, two ribonucleases with high sequence identity and (2) dissecting the difference in the energetic (e.g., steric and electrostatic) contribution of specific residues involved in RI-binding to design rationally-based RNase 1 variants. One of the outcomes of this design strategy was engineering cytotoxic RNase 1 variants with at least $10^7$-fold lower affinity and 2700-fold lower association rate for hRI than wild-type RNase 1.

Differences in Pancreatic Ribonuclease Recognition by RI

The fast atomic density evaluator (FADE) algorithm revealed regions of high shape complementarity between pRI and RNase A. By inserting disruptive mutations in regions identified to have high shape complementarity, D38R/R39D/N67R/G88R RNase A ($K_d$=510 nM for hRI) and C31A/C32A/G38R/K39D/G88R BS-RNase ($K_d$=110 nM for hRI) were developed that had significantly decreased affinities for RI. Using the same logic and shape complementarity regions, we designed G38R/R39G/N67R/N88R RNase 1 (Table 5). When applied to RNase 1, this strategy failed to reduce the affinity of hRI for RNase 1. The binding affinity of hRI for this quadruple variant of RNase 1 was near the affinity of hRI for wild-type RNase 1 Consequently, we wanted to determine what separated the RI recognition of RNase 1 from RNase A.

Residue 39. Arg39 of RNase A had the highest shape complementarity score for pRI•RNase A and was proposed to be a secondary anchor residue. When Arg39 was mutated to aspartate in G88R RNase A to create R39D/G88R RNase A, the R39D mutation instilled 725-fold lower RI affinity In RNase 1, Arg39 has even lighter interactions with hRI with the formation of 3 hydrogen bonds and consequently the energetic contribution of R39D is second highest among the residues studied at ΔΔΔG=2.2 kcal/mol.

Similar to RNase A, a mutation of Arg39 to Asp decreases the affinity of hRI for RNase 1, but the cytotoxicity of variants with R39D is proportionally lower than other variants with similar RI evasion. Part of the negative influence of an R39D substitution on the cytotoxicity of RNase 1 variants can be accounted for by the 3-fold decrease in the catalytic activity, but the increased activity does not completely account for the high cytotoxicity of N67D/N88A/G89D/R91D RNase 1. The disproportionately large decrease in cytotoxicity in variants of RNase 1 with R39D advocates a role for Arg39 in cell surface binding. Arg39 is positioned between two positively charged patches on RNase 1 (FIG. 5) and so a negative charge at position 39 may weaken the cell surface binding of both positive patches, producing a proportionally greater decrease in internalization and cytotoxicity.

Residue 67. Previously, the recognition of Asn67 by hRI was exploited to develop RI variants that selectively bind to angiogenin but not RNase 1 or RNase A.[18] By incorporating a tryptophan at positions 408 and 410 in hRI, a highly selective variant of hRI was engineered that only bound angiogenin. A tryptophan substitution at Asn67 of RNase 1 to sterically hinder the binding of residues 408-410 in hRI did not produce a comparable binding change (data not shown). Yet, an aspartate at position 67 does destabilize the complex by 1.9 kcal/mol (Table 5).

Figure 2:
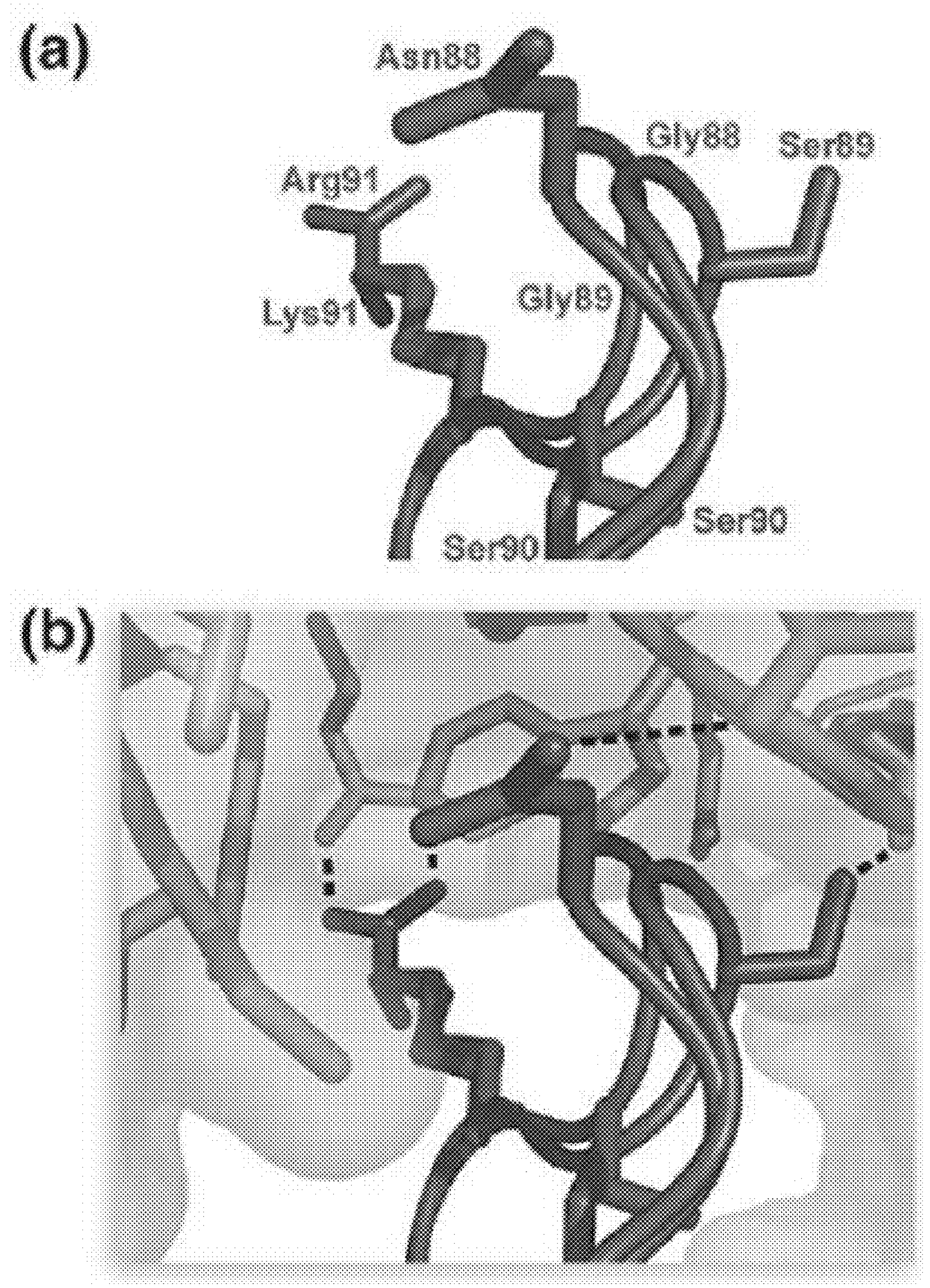
FIGS. 2A-B show a color-coded comparison or the β4-β5 loop in RNase 1 and RNase A when bound to RI.

Asn67 was proposed to be a primary anchor residue in the pRI-RNase A interface, due to its burial of surface area and its lack of molecular motion.[22] In agreement with the assertion that Asn67 plays a role in complex formation, we find that the energetic destabilization caused by mutation at position 67 is substantial ($\Delta\Delta\Delta G$=1.9 kcal/mol). However, Arg39 and Arg91 provide more overall energy to stabilization of the hRI•RNase 1 complex.

β4-β5 loop. To determine what separated the RI recognition of RNase 1 from RNase A in the β4-β5 loop region, a 3-D structural comparison was performed as shown in FIG. 2 between the β4-β5 loop in RNase 1 (purple) and RNase A (blue) when bound to RI (green). This was accomplished by aligning the alpha-carbons of RNase 1 and RNase A with the program Sequoia, and images were created with the program PyMOL. (A) Structure of β4-β5 loops, with RI concealed. Side chains of residues 88-91 are shown as sticks. Amino acids are labeled with the color corresponding to the color of the ribonuclease. (B) Orientation of the β4-β5 loop bound to RI. RNase A (chain E) was aligned to RNase 1 (chain Z) and then modeled into hRI (chain Y) based on the alignment to RNase 1. Hydrogen bonds are shown as dotted lines. Hydrogen bonds between hRI and RNase A are hypothesized based on the alignment of hRI and pRI.

By performing this comparative alignment, we discovered that in contrast to prior results, where Gly 88 to arginine mutations decreased the affinity of pRI for RNase A by $10^4$ M and the affinity of BS-RNase for hRI by 250-fold, substituting Asn88 with arginine in RNase 1 did not generate a similar decrease in affinity. In the crystal structure of the hRI•RNase 1 complex, the β4-β5 loop adopts a similar conformation to RNase A with pRI (FIG. 2). One major difference between RNase 1 and RNase A in the β4-β5 loop is with residue 88 where Asn88 of RNase 1 hydrogen bonds with Glu264 instead of folding into the pocket formed by Trp261 and Trp263 like Gly88 in RNase A. Asn88 in RNase 1 is located on the outer surface of the hRI•RNase 1 interface and could accommodate the structural bulk of an arginine or carbohydrate chain while still maintaining high affinity for RI.

Gly89 of RNase 1 has been proposed to constitute the structural analogue of Gly 88 in RNase A, but mutational studies at Gly89 in RNase 1 have, also, failed to produce variants with lower affinity for RI. Gly89 in RNase 1 overlays more closely with Ser89 in RNase A (FIG. 2), but Gly89 is unable to hydrogen bond with Glu206 as seen for Ser89 in RNase A.

Gly89 in RNase 1 still has van der Waals contact with Trp261 and Trp263 in hRI•RNase 1, but Gly 89 appears to have greater flexibility than Gly88 in RNase A. Consequently, hRI can adjust to an aspartate or arginine substitution at Gly 89 in RNase 1 while maintaining near wild-type affinity (FIG. 2).

Among the five residues investigated, Arg91 had the greatest energetic influence on the hRI•RNase 1 complex ($\Delta\Delta G$=2.8 kcal/mol). Arg91 contacts hRI in the negatively-charged bend of the hRI surface (FIG. 5), where Arg91 forms two hydrogen bonds with Glu287of hRI. Lys91 in RNase A was proposed to play a secondary latching role in anchoring RNase A to pRI, but in RNase 1, Arg91 may serve as a primary anchor residue to recognition by hRI.

Substituting Arg91 with an aspartate severed the tight hydrogen bonds to Glu287of hRI, and replaced the attractive force of Arg91 with an electrostatic repulsion. This loss of charge-charge attraction and gain of electrostatic repulsion at position 91 caused the largest change in the overall binding affinity.

Electrostatic Anchor Residues

In a survey of 14 enzyme-inhibitor complexes, all fourteen complexes had a positive $\Delta G_{elec.}$[3] meaning electrostatics were a negative force to complex formation. However, RI•RNase complexes are atypical protein-protein interfaces. Binding of angiogenin to hRI has an electrostatic energy of interaction of −12.3 kcal/mol and a calculated rate increase due to electrostatics of $10^6 M^{-1} s^{-1}$. In contrast to other complexes, in RI•RNase complexes electrostatics play a key role in binding.

Figure 3:
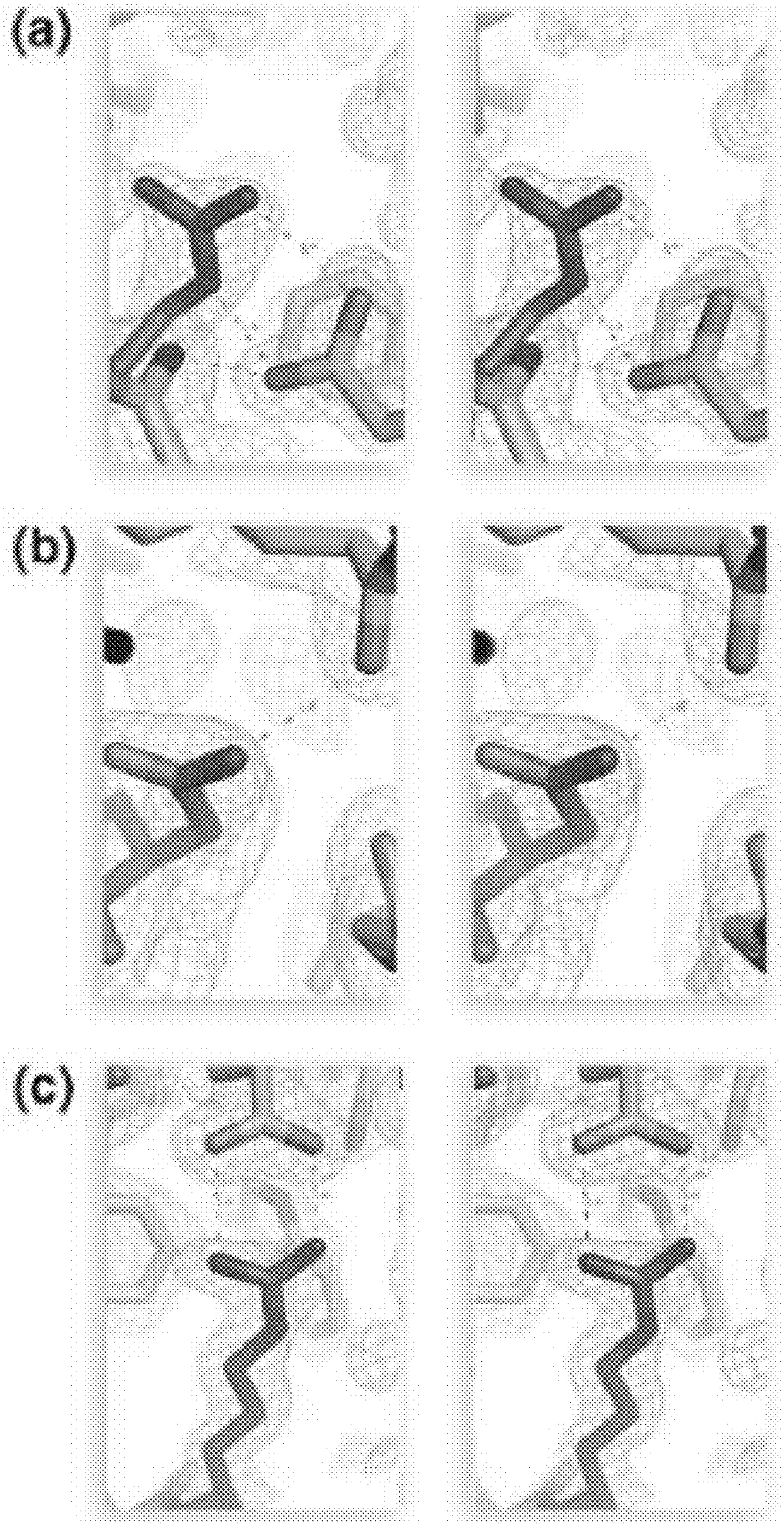
FIGS. 3A-C show electron density at 1σ of key shape complementarity residues between hRI and RNase 1.

FIG. 3 shows electron density at 1σ of key shape complementarity residues between hRI (green) and RNase 1 (purple). Specific residues shown in detail are (A) Arg39, (B) Asn67, and (C) Arg91. Highlighted regions are shown in wall-eyed stereo and interprotein hydrogen bonds are displayed by black dotted lines. Images were created with the program PyMOL, FIG. 3 demonstrates that instead of sterically-constrained residues making initial contact with hRI, the electrostatics of key solvent exposed charged residues like Arg39 and Arg91 drive the association rate.

Specifically. Arg39 and Arg91 contributes at least 0.3 kcal/mol more to the binding energy than Asn67, Asn88, or Gly89 do. The charged surface of Arg39 and Arg91 determines the association rate as substitution of these charges to leucine in R39L/N67L/N88A/G89L/R91L RNase 1 decreases the association rate by 110-fold. Hence, Arg39 and Arg91 serve a special role in the hRI•RNase 1 complex that we define as electrostatic anchor residues. A residue that anchors the formation of a protein-protein complex should provide the major energetic force to complex formation and be the major marker for the recognition of its protein-binding partner.

Figure 5:
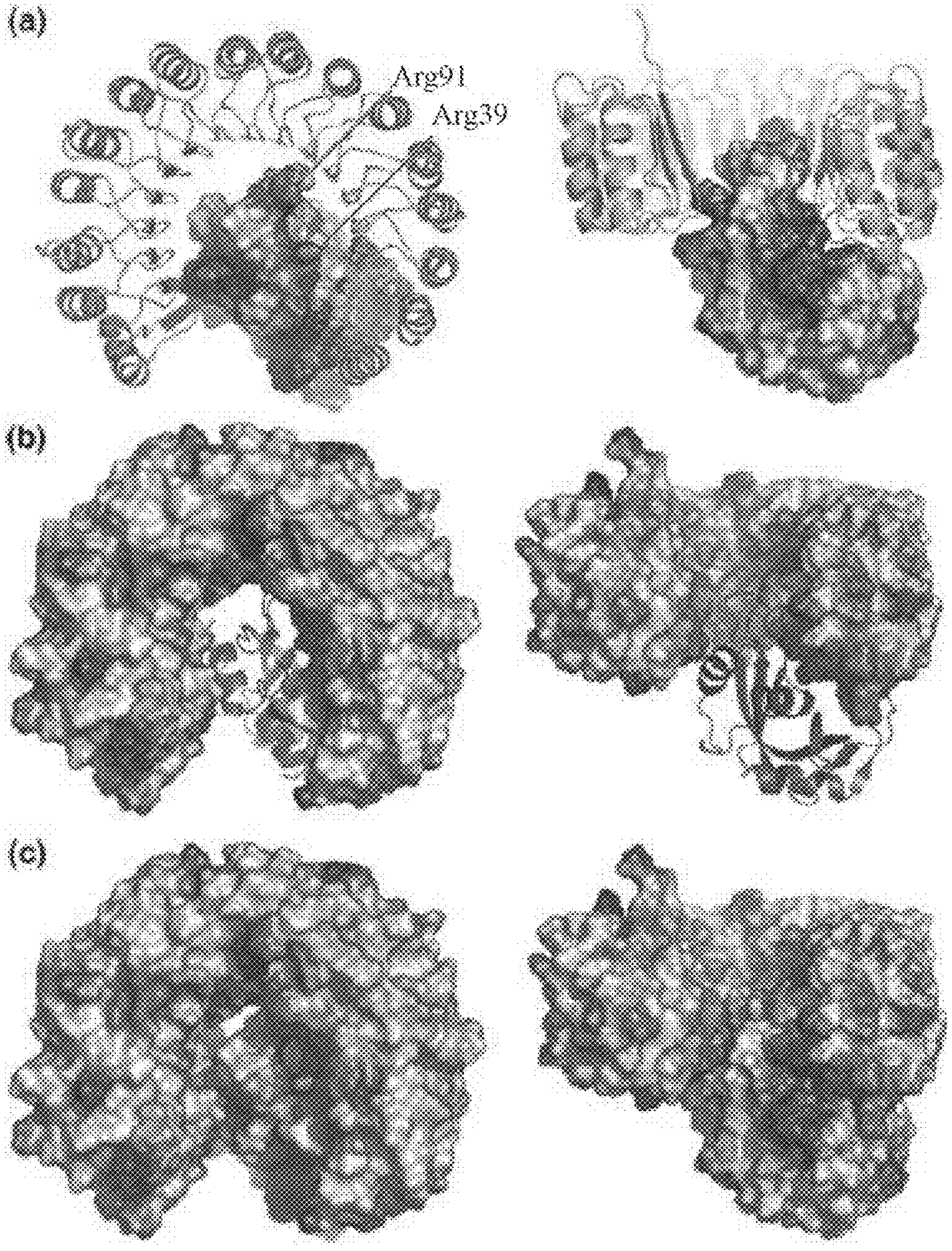
FIGS. 5A-C show an electrostatic representation of the hRI and RNase 1 interaction.

Electrostatic residues like Arg39 and Arg91 fit these criteria, as they are initially recognized by the electrostatic surface of hRI (FIG. 5). Specifically, FIG. 5 illustrates an electrostatic representation of the hRI (green) and RNase 1 (purple) interaction. Protein contact potential of RNase 1, residues 39 and 91 are labeled (A), hRI (B), and hRI•RNase 1 (C) as shown. The intensity of the blue (positive) and red (negative) coloration is indicative of the local electrostatic environment. Vacuum electrostatics were calculated and images were created with the program PyMOL.

Furthermore, electrostatic residues Arg39 and Arg91 strongly affect the association rate of the complex (Table 6). Thus, Arg39 and Arg91 keep RNase 1 bound to hRI through tight hydrogen bonds (FIG. 3), allowing other contacts in the complex to form. Arg39 and Arg91 steer the formation of the hRI•RNase 1 complex over longer distances than the sterics of Asn67 and ultimately contribute more binding energy to the affinity of the hRI•RNase 1 complex. Although, Arg39 and Lys91 in RNase A were proposed to play a role in RI binding, the key function that the electrostatics of these residues supply to the hRI•RNase 1 complex was underestimated.

Energetics of Evasion

Charged amino acids constitute 19% of all exposed amino acids on a protein surface, but in the average protein-protein interface fewer charged residues are exposed. Charge-charge interactions in protein-protein interfaces are disfavored energetically by a large energetic penalty to desolvate the exposed charge residue upon binding. The energetic penalty of desolvation can be circumvented by leaving key charge interactions partially solvent exposed upon complex formation. In FIG. 3, the electron density for multiple solvent molecules are visible surrounding important charged interactions between hRI and RNase 1. RI seems to use its unusual horseshoe-shape to expose greater surface area to solvent and only partially desolvate key charged residues. This exposure to solvent diminishes the energetic desolvation penalty incurred by RI upon RNase 1 binding and allows electrostatics to remain a driving energetic force to complex formation.

The positive charge on the RNase 1 surface (FIG. 5) facilitates substrate binding and consequently is necessary to maintain the biological activity of RNase 1. RI takes advantage of the necessity for a charged surface on RNase 1 to tightly and rapidly inhibit RNase 1 using long range electrostatics. FIG. 5 highlights the positive and negative charge distribution on RNase 1 and hRI, respectively. In the crystal structure, both Arg39 and Arg91 are tightly enclosed in the negative inner surface of RI (FIG. 5) and anchor RNase 1 to the negative surface of hRI.

By incorporating negatively-charged aspartate residues at key electrostatic anchors, we have lowered the equilibrium dissociation constant of hRI for RNase 1 by nearly seven orders of magnitude. Comparison of variants of RNase 1 with mutations at Arg39 and Asn67 illustrate how electrostatics help in the evasion of RI binding. The electrostatic repulsion of an aspartate at positions 39 and 67 destabilizes the complex by 2.2 and 1.9 kcal/mol, respectively (Table 5). If instead of an aspartate residue, the wild-type residue is changed to glycine at residue 39 and arginine at residue 67 (G38R/R39G/N67R/N88R RNase 1), a similar destabilization of the complex is not observed (total ΔΔG=3.0 kcal/mol). Thus, the electrostatics of residues Arg39 and Asn67 play a large role in determining the affinity of an RNase 1 variant.

Overall, the repulsion of RI binding by aspartate substitutions in RNase 1 is superadditive as the binding energy lost by the reversion of single mutations in R39D/N67D/N88A/G89D/R91D RNase 1 (8.2 kcal/mol) is less than the binding energy lost with R39D/N67D/N88A/G89D/R91D RNase 1 (9.3 kcal/mol). Examples of superadditive mutations in protein-protein complexes are uncommon, but have been observed with hRI•angiogenin. The superadditive results for hRI•RNase 1, however, are surprising, because previous mutations in hRI•RNase A were superadditive. The superadditivity of the mutations to the hRI•RNase 1 complex can be explained partially by the methods and partially by the type of mutations. By combining multiple substitutions in RNase 1, the native RNase 1 structure may have been contorted such that additional mutations develop disruptive contacts with RI that are not seen for single mutants. Also, the electrostatic repulsion of an aspartate substitution instead of an alanine substitution can perturb a larger surface area and increase the energetic destabilization of the mutation. For example, the ΔΔΔG values for all four aspartate substitutions in RNase 1 are larger than the ΔΔΔG value for deleting a single hydrogen bond (Asn88 to Ala88) (Table 5). Overall, we exploited the tight electrostatic attraction between hRI and RNase 1 to develop variants of RNase 1 with comparable affinity to the most evasive RNase A variants.

Rates of Association and Dissociation

Electrostatics steer the formation of protein-protein complexes over long distances and increase the rate of association over diffusion limited processes. We measured the difference in the kinetic rate constants between two variants of RNase 1 from Table 5 to determine which kinetic constant led to the increased evasion of R39D/N67D/N88A/G89D/R91D RNase 1. Overall, changes in the dissociation rate (3100-fold) and association rate (2700-fold) constants of R39D/N67D/N88A/G89D/R91D RNase 1 each account for half the decreased affinity for hRI as compared to wild-type RNase 1 (Table 6). The important contribution of the association rate to the micromolar affinity of R39D/N67D/N88A/G89D/R91D RNase 1 is seen more clearly when its rates are compared to R39L/N67L/N88A/G89L/R91L RNase 1 (Table 6).

The 50-fold increased RI-evasion of R39D/N67D/N88A/G89D/R91D RNase 1 over R39L/N67L/N88A/G89L/R91L RNase 1 is almost completely driven by long-range electrostatic repulsion through its effect on the association rate. The total influence of the electrostatics of residues 39, 67, 88, 89, and 91 on hRI•RNase 1 complex formation can be approximated by combining the 110-fold decrease in association rate due to the loss of attractive forces by leucine substitutions and the 25-fold decrease in association rate with the gain of repulsive forces by aspartate substitutions. Overall, electrostatics contributes 2700-fold to the decreased affinity of R39D/N67D/N88A/G89D/R91D RNase 1 for hRI and the experimental results here reinforce previous calculations on the importance of electrostatics in the binding of RI to ribonucleases. The example of hRI•RNase 1 demonstrates that proteins have evolved an additional strategy, using electrostatic anchor residues, for recognizing their protein partner in solution when charge strongly influences the association rate.

These results demonstrate that cytotoxic variants of human RNase 1 are quite possible to construct based on the data revealed here. We anticipate that consideration of the atomic coordinates of the hRI•RNase 1 complex can lead to even more cytotoxic variants of RNase 1.

2. Detailed Methods and Materials

Materials: *Escherichia coli* BL21 (DE3) and pET22b(+) were from Novagen (Madison, Wis.). The fluorogenic ribonuclease substrate, 6-FAM-dArU(dA)2-6-TAMRA, was from Integrated DNA Technologies (Coralville, Iowa). Enzymes were from Promega (Madison, Wis.). K-562 cells were from the American Type Culture Collection (Manassas, Va.). Cell culture medium and supplements were from Invitrogen (Carlsbad, Calif.). [methyl-3H]Thymidine (6.7 Ci/mmol) was from Perkin-Elmer (Boston, Mass.). HiTrap NHS-ester columns were from Amersham Biosciences (Piscataway, N.J.). RNase A Type III-A for attachment to HiTrap NHS-ester columns was from Sigma-Aldrich (St. Louis, Mo.). MES buffer (Sigma-Aldrich, St. Louis, Mo.) was purified by anion exchange chromatography to remove trace amounts of oligomeric vinylsulfonic acid. All other chemicals were of commercial grade or better, and were used without further purification. Terrific Broth (TB) contained (in 1.00 L) tryptone (12 g), yeast extract (24 g), glycerol (4 mL), KH2PO4 (2.31 g), and KH2PO4 (12.54 g). Phosphate-buffered saline (PBS) pH 7.4 contained (in 1.00 L) NaCl (8.0 g), KCl (2.0 g). Na2HPO4.7H20 (1.15 g), KH2PO4 (2.0 g), and NaN3 (0.10 g).

Instrumentation: Fluorescence measurements were made with a QuantaMaster1 photoncounting fluorimeter with sample stirring (Photon Technology International, South Brunswick, N.J.). Thermal denaturation data were collected using a Cary 3 double-beam spectrophotometer equipped with a Cary temperature-controller (Varian, Palo Alto, Calif.). [methyl-3H]Thymidine incorporation into genomic DNA was quantified by liquid scintillation counting using a Microbeta TriLux liquid scintillation and luminescence counter (Perkin-Elmer, Wellesley, Mass.). The mass of RNase 1 and its variants was confirmed by matrix-assisted laser desorption/ionization time-of-flight (MALDI-TOF) mass spectrometry using a Voyager-DEPRO Biospectrometry Workstation (Applied Biosystems, Foster City, Calif.).

RNase 1 purification: RNase 1 was purified from inclusion bodies using the same oxidative refolding procedure described previously.[19] Variants of RNase 1 were created by Quikchange site-directed mutagenesis or Quikchange Multi site-directed mutagenesis (Stratagene, La Jolla. CA) following the manufacturer's protocol. Variants were purified using the same procedure used for wild-type RNase 1.[19] Variants of RNase 1 with free cysteine residues at position 19 were protected with 5,5'-dithio-bis(2-nitrobenzoic acid) (DTNB) before fluorophore attachment. Then, immediately before use, TNB-protected variants were deprotected using a three-fold molar excess of dithiothreitol (DTT) and desalted by chromatography using a PD-10 desalting column (Amersham Biosciences, Piscataway, N.J.). RNase 1 conjugates with 5-iodoacetamido fluorescein (Sigma-Aldrich, St. Louis, Mo.) were prepared by reaction with a ten-fold molar excess of 5-iodoacetamido fluorescein for 4-6 h at 25° C. Conjugates were purified by chromatography using a HiTrap SP FF column. The molecular masses of RNase 1 and its variants were confirmed by matrix-assisted laser desorption/ionization time-of-flight (MALDI-TOF) mass spectrometry using a Voyager-DEPRO Biospectrometry Workstation.

hRI purification: hRI was purified similarly to procedures described previously. Briefly, a pET-22b(+) plasmid that contained cDNA for hRI was transformed into *E. coli* BL21 (DE3) and a single colony was used to inoculate LB medium (25 mL) containing ampicillin (150 µg/mL). A starter culture was grown for 16 h at 37° C. and 250 rpm and was used to inoculate cultures of TB medium (1.00 L) containing ampicillin (200 µg/mL).

These cultures were grown at 37° C. and 225 rpm until $OD_{o00}$>3.0. Expression of the hRI cDNA was induced by adding IPTG (0.5 mM) and growing for 16 h at 18° C. and 225 rpm. Bacteria were collected by centrifugation (12,000×g for 10 min) and resuspended in 30 mL of 50 mM Tris-HCl buffer, pH 7.5, containing EDTA (10 mM) and DTT (10 mM). Bacteria were lysed by two passes through a French pressure cell, and the cellular debris was removed by ultracentrifugation. RNase A was attached covalently to the resin in two 5-mL HiTrap NHS-ester columns, following the manufacturer's protocol. The supernatant was loaded onto these two columns connected in series. The peak eluted from the RNase A affinity columns was dialyzed for 16 h against 4 L of 20 mM Tris-HCl buffer, pH 7.5, containing DTT (10 mM) and EDTA (1 mM) and purified further by chromatography using a HiTrap Q column.[46] The purity of the eluted hRI was shown to be > 99% by SDS-PAGE (data not shown).

Complex purification: Purified RNase 1 (50 mg/mL) and hRI (10 mg/mL) were mixed at a molar ratio of 1.2 to 1.0, respectively. This solution was incubated at 25° C. for 60 min to allow for complex formation. The complex was loaded onto a 5-mL HiTrap Q column that had been pre-equilibrated with 20 mM Hepes-NaOH buffer, pH 7.5, containing DTT (10 mM) and glycerol (2% v/v). The complex was eluted with a linear gradient of NaCl (0-0.4 M) over 30 column volumes. Free RNase 1 eluted with the flowthrough, and the hRI•RNase 1 complex eluted at about 0.15 M NaCl. Purified complex was dialyzed for 16 h at 4° C. against 20 mM Hepes-NaOH buffer, pH 7.5, containing DTT (10 mM) and glycerol (2% v/v). Finally, the complex was concentrated in a Vivaspin 20 mL centrifugal concentrator (Vivascience AG, Hannover, Germany) at 6,000×g to a final concentration of 10 mg/mL. Aliquots were flash frozen and stored at −80° C.

Crystallization: Crystals of the hRI•RNase 1 complex were obtained by hanging-drop vapor diffusion in 20 mM sodium citrate buffer, pH 4.2, containing methyl ether PEG 2000 (10% w/v), ammonium sulfate (1 mM), and DTT (25 mM) with the hanging drop solution containing a mixture of purified hRI RNase 1 (0.9 µL) and citrate buffer solution (5.1 µL). Diffraction-quality crystals grew within a week at 25° C. Protein crystals were soaked in reservoir solutions containing increasing amounts of ethylene glycol up to 25% (v/v), and were flash-cooled in a stream of cryogenic $N_2$(g).

Diffraction data were collected at SER-CAT Sector 22 at Argonne National Laboratories. The crystal was maintained at 100 K during data collection, and X-rays were tuned to a wavelength of 0.99997 Å. The diffraction images were integrated and scaled using HKL2000. The phases were determined through molecular replacement using MOLREP from the CCP4 suite with PDB entry 1DFJ as the starting model. Arp-Warp[50] was used to build the initial model, which was then completed with alternate cycles of model building with Xfit[51] and refinement using REFMAC. The structural coordinates for the x-ray structure of human ribonuclease inhibitor complexed with ribonuclease inhibitor have been deposited in the Protein Data Bank (PDB) having an accession or identification No. 1Z7X, incorporated by reference herein in its entirety.

Ribonucleolytic activity: The ribonucleolytic activity of RNase 1 and its variants was quantitated using 6-FAM-dArU $(dA)_2$-6-TAMRA. Cleavage of this substrate at the uridine ribonucleotide leads to a 180-fold increase in fluorescence Assays were carried out at 23(±2)° C. in 2 ml of 0.10 M Mes-NaOH buffer, pH 6.0, containing NaCl (0.10 M). Fluorescence data were fitted to the equation: $k_{cat}/K_M=(\Delta I/\Delta t)/((I_f-I_0)[E])$ where ΔI/Δt represents the initial reaction velocity, $I_0$ is the fluorescence intensity before the addition of a ribonuclease, $I_f$ corresponds to final fluorescence after complete substrate hydrolysis, and [E] is the total ribonuclease concentration.

Conformational stability: The conformational stability was determined by following the change in absorbance at 287 nM with increasing temperature. The temperature of PBS containing a ribonuclease (0.1-0.2 mg/mL) in PBS was raised from 20 to 80° C. at 0.15° C./min. The $A_{287}$ was followed at 1° C. intervals and the absorbance change were fitted to a two-state model of denaturation, in which the temperature at the midpoint of the transition curve corresponds to $T_m$.

RI evasion: The affinity of RNase 1 variants for hRI was determined by using a fluorescent competition assay reported previously with minor modifications. Briefly 2.0 mL of PBS containing DTT (5 mM), fluorescein-labeled G88R RNase A (50 nM), and an unlabeled RNase 1 variant was incubated at 23 (±2)° C. for 20 min. The initial fluorescence intensity of the unbound fluorescein-labeled G88R RNase A was monitored for 3 min (excitation: 491 nm; emission: 511 nm) hRI was then added to 50 nM and the final fluorescence intensity was measured. Values for $K_d$ were obtained by nonlinear least-squares analysis of the binding isotherm using the program DELTAGRAPH 5.5 (Red Rock Software, Salt Lake City, Utah). The $K_d$ value for the complex of hRI and fluorescein-labeled G88R RNase A is 1.4 nM.

Kinetic assay: The dissociation rate constant for complexes of hRI and variants of RNase 1 were determined by a procedure similar to that described previously. Briefly, equimolar concentrations of hRI and fluorescein-labeled RNase 1 variant were allowed to reach equilibrium in PBS containing DTT (5 mM). The equimolar concentrations were 20-fold greater than the previously determined $K_d$ value for each hRI•RNase 1 complex. After reaching equilibrium, a 100-fold molar excess of wild-type RNase A (Sigma-Aldrich) was added to scavenge free hRI. The increase in fluorescence was followed as the hRI•RNase 1 variant complex dissociated irreversibly. To calculate the dissociation rate constant, $k_d$, the data were fitted to eq 1, wherein $F_0$ is the fluorescence before the addition of wild-type RNase A and $F_{00}$ is the fluorescence after complete dissociation of the complex.

$$F=F_0+(F_{00}-F_0)(1-e^{kdt}) \quad (1)$$

Cytotoxicity: The effect of RNase 1 and its variants on the proliferation of K-562 cells was assayed as described previously. Briefly, after a 44-h incubation with ribonuclease, K-562 cells were treated with [methyl-$^3$H]thymidine for 4-h and the incorporation of radioactive thymidine into the cellular DNA was quantified by liquid scintillation counting. Results are shown as the percentage of [methyl-$^3$H]thymidine incorporated into the DNA as compared to the incorporation into control K-562 cells where only PBS was added. Data are the average of three measurements for each concentration, and the entire experiment was repeated in triplicate. Values for $IC_{50}$ were calculated by fitting the curves using nonlinear regression to eq 2, wherein y is the total DNA synthesis following the [methyl-$^3$H]thymidine pulse, and h is the slope of the curve.

$$y = \frac{100\%}{1 + 10^{(\log(IC_{50}) - \log[ribonuclease])h}} \quad (2)$$

RESULTS

Important Interactions Between hRI and RNase 1

RNase 1 and RNase A share 70% sequence identity, but previous mutagenesis studies have suggested a variation in how they are recognized by RI. To structurally elucidate these differences in RI binding, crystals of the hRI•RNase 1 complex were grown under low ionic conditions as described herein below. The structure was refined to an R-value of 0.175 (R-free 0.236) and at a resolution of 1.95 Å (Table 1).

TABLE 1

| Crystallographic, data processing, and refinement statistics. | |
|---|---|
| Data Collection Statistics | Native |
| Space Group | P212121 |
| Unit Cell Parameters | a = 71.338, b = 107.546, c = 155.036 |
| alpha beta gamma | 90.00 90.00 90.00 |
| Energy (keV) | 12.399 |
| Wavelength (Å) | 0.99997 |
| Overall Resolution Range (Å) | 47.17-1.95 (2.00-1.95) |
| Number of Reflections | Measured 573939, Unique 84446 |
| Completeness (%) | 97.0 (72.6) |
| Rmerge[a] | 0.078 (0.424) |
| Redundancy | 6.8 (3.6) |
| Mean I/σ (I) | 16.96 (2.94) |
| Phasing | |
| MR Correlation Coefficient | |
| (MOLREP) | 0.223 |
| MR Model | IDFJ |
| Refinement and Model Statistics from REFMAC 5.2.0005 | |
| Data Set | Native |
| Number of reflections (Total) | 80141 |
| Number of reflections (Free) | 4225 |
| $R_{cryst}^{b}$ ($R_{free}^{c}$) | 0.175 (0.236) |
| RMSD bonds (Å) | 0.016 |
| RMSD angles (°) | 1.515 |

TABLE 1-continued

| Crystallographic, data processing, and refinement statistics. | |
|---|---|
| ESU based on $R_{free}$ (Å) | 0.166 |
| Average B factor (Å$^2$) | 28.04 |
| Number of water molecules | 854 |
| Ramachandran plot | |
| Residues in most favorable region | 86.8% |
| Residues in additional allowed region | 12.8% |
| Residues in generously allowed region | 0.4% |
| Residues in disallowed region | 0.0% |

Values in parentheses refer to the highest resolution shell.

[a]$R_{merge} = 3_h 3_i *I_i(_h) - \langle I(h)\rangle / 3_h 3_i /_i(h)$, where $I_i$(h) is the intensity of an individual measurement of the reflection and <I(h)> is the mean intensity of the reflection.

[b]$R_{cryst} = 3_h **F_{obs}* - *F_{calc} * */3_h*/F_{obs}*$, where $F_{obs}$ and $F_{calc}$ are the observed and calculated structure-factor amplitudes, respectively.

[c]$R_{free}$ was calculated as $R_{cryst}$ using 5.0% of the randomly selected unique reflections that were omitted from structure refinement.

Tables 2, 3, and 4 summarize some of the results of the analysis of the raw data, which was included in Appendix A of the corresponding U.S. priority application Ser. No. 60/691,311. The atomic coordinates were also submitted to the protein Data Bank (Accession No. 1Z7X). Table 3 lists data from the analysis of the interaction between hRI and RNase 1, and identifies those amino acid residues in the human RNase 1 structure which are less than 3.20 Angstroms from amino acid residues in hRI when RNase 1 is bound to hRI. The distance of 3.20 Angstroms is a maximal distance for the existence of a meaningful interaction between the two molecules and thus indicates residues in RNase 1 that can be substituted to alter the interaction between the two molecules. This list includes several of the residues, the variations in which have demonstrated conversion of RNase A into a cytotoxic molecule, notably residue 88.

TABLE 2

| RNase 1 Residues ≦3.20 Å from hRI Residues in hRI•RNase 1 Complex | |
|---|---|
| Arg4 | Pro42 |
| Lys7 | Lys66 |
| Gln11 | Asn71 |
| Arg31 | Asn88 |
| Arg32 | Arg91 |
| Arg39 | Glu111 |
| Lys41 | |

Tables 3 and 4 list the locations of closest interaction between hRI and human RNase 1, as revealed by analysis of the atomic locations of the molecules in the two distinct molecular complexes (W—X and Y—Z) that formed the crystal used in the structural analysis below. The 3-D structures of these two molecular complexes were similar, but not identical, as can be seen from Table 3 and Table 4.

TABLE 3

| W•X Complex | | |
|---|---|---|
| RNase 1 (X) atom | hRI (W) atom | distance (Å) |
| Arg4 NH1 | Ala441 CB | 2.33 |
| Lvs7 CE | Ser461 OXT | 3.18 |
| Gln11 NE2 | Ser461 OXT | 3.05 |
| Arg31 NH1 | Gln11 OE1 | 2.78 |
| Arg31 NH2 | Arg34 NH1 | 2.89 |
| Arg32 NE | Asp37 OD2 | 2.78 |
| Arg39 NE | Glu402 OE2 | 2.39 |
| Arg39 NE | Trp376 CH2 | 3.11 |
| Lys41 CE | Asp436 OD1 | 2.83 |
| Lys66 NZ | Asn407 OD1 | 2.87 |
| Asn71 ND2 | Tyr438 OH | 2.61 |

TABLE 3-continued

| W•X Complex | | |
|---|---|---|
| RNase 1 (X) atom | hRI (W) atom | distance (Å) |
| Asn88 OD1 | Glu265 OE2 | 2.72 |
| Arg91 NH2 | Glu288 OE2 | 2.65 |

TABLE 4

| Y•Z Complex | | |
|---|---|---|
| RNase 1 (Z) atom | hRI (Y) atom | distance (Å) |
| Lys7 NZ | Glu444 OE2 | 3.18 |
| Arg32 NE | Asp37 OD1 | 2.63 |
| Arg39 NE | Glu402 OE2 | 2.79 |
| Lys41 NZ | Asp436 OD1 | 2.68 |
| Pro42 CG | Asn407 ND2 | 3.17 |
| Lys66 CE | Cys409 SG | 3.20 |
| Asn71 ND2 | Tyr438 OH | 2.86 |
| Asn88 OD1 | Glu265 OE2 | 2.70 |
| Arg91 OD1 | Glu288 OE2 | 2.60 |
| Glu111 OE2 | Tyr438 OH | 2.58 |

From this summary of the raw data, it can be understood that amino acid residues Arg39, Asn88, and Arg91 represent prime locations for modifying RNase 1 to interfere with the binding of hRI. As a result, RNase 1 would be able to evade the action of the inhibitor in vivo and increase cytotoxicity of RNase 1 for chemotherapeutic purposes.

The contacts from both chains of RNase 1 in the unit cell are provided in FIG. 1A The secondary structure of RNase A is identified with h (α-helix), s (β-strand), or t (turn). Residues in van der Waals or hydrophobic contact with RI are in blue. Residues with hydrogen bonds to RI are in red. Conserved cysteine residues are in yellow. Key catalytic residues are in black boxes. In chain X of RNase 1 (FIG. 1*a*), a bound citrate molecule forms tight hydrogen bonds to all three catalytic residues, His 12, His 118 and Lys41. The bound citrate perturbs the substrate binding cleft of RNase 1 causing Arg10 and Lys66 to undergo significant conformational changes. Lys66 in chain X forms a hydrogen bond to Asn406 of hRI. However, in chain Z (FIG. 1B, 3-D structure of RNase 1 chain Z from 1Z7X), only van der Waals interactions were observed with hRI. Residues are colored using the same scheme as in the sequence alignment in FIG. 1A, except that active-site residues are not highlighted. The image was created with the program PyMOL (DeLano Scientific, South San Francisco, Calif.). To facilitate comparison between the structures of hRI•RNase 1 and pRI•RNase A,[15] chains Y (hRI) and Z (RNase 1) (without citrate bound) serve as the hRI•RNase 1 complex for comparison.

The root mean square deviation (rmsd) between the alpha carbons of hRI•RNase 1 and pRI•RNase A is 2.8 Å. Much of the deviation between the complexes originates from the alignment of pRI with hRI (rmsd=1.6 Å), because unlike hRI, pRI is observed to undergo a conformational change upon RNase A binding. The alpha carbons of RNase 1 and RNase A have less deviation (rmsd=0.6 Å). Angiogenin and EDN, the other human ribonucleases crystallized with hRI, gave rmsd values of 7.4 and 6.3 Å from RNase 1, respectively. The considerably higher rmsd for angiogenin and EDN shows the structural variation among human ribonucleases and underscores the similarity between RNase 1 and RNase A.

Figure 1B:
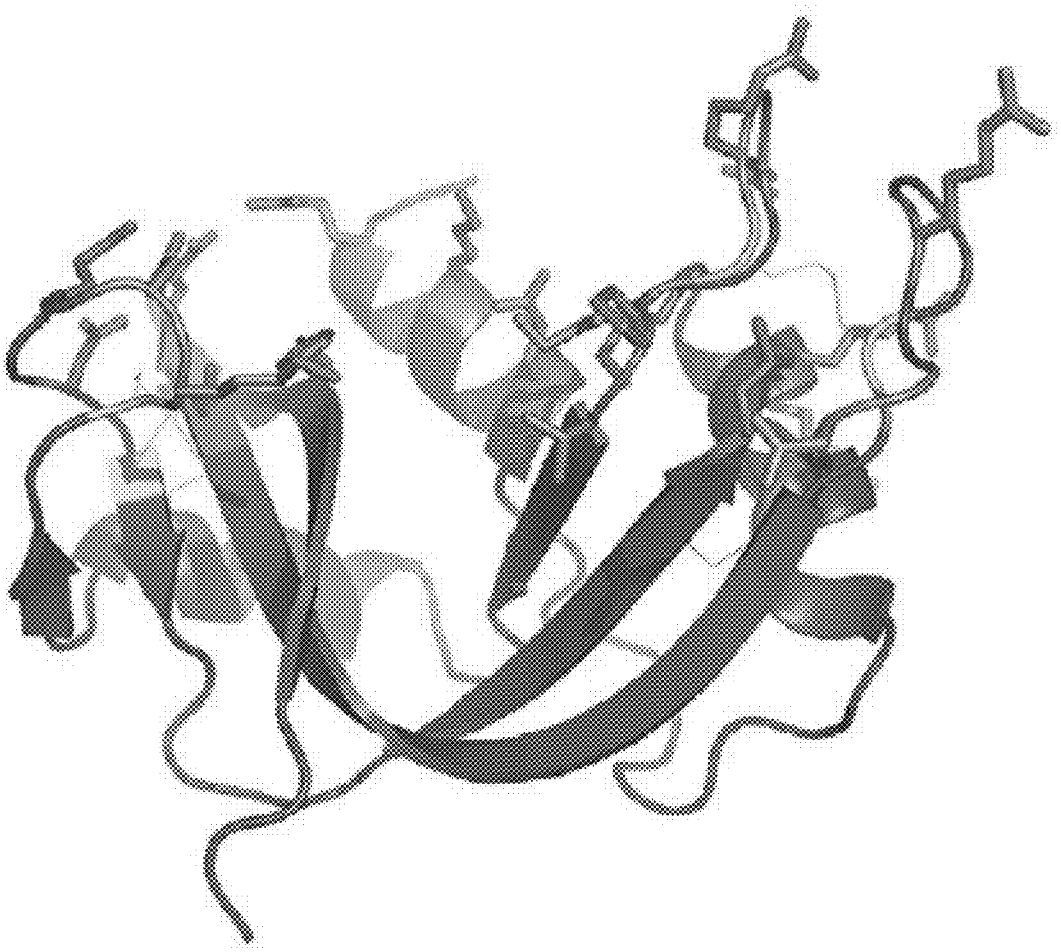

The conservation of contact residues between the complexes of hRI•RNase 1 and pRI•RNase A is shown in FIG. 1A. The localization of RI-contact residues on the active-site face of RNase 1 is shown in FIG. 1B. The total number of contact residues (23) with RI is conserved between RNase 1 and RNase. A divergence in the recognition of RNase 1 and RNase A by RI is in the number of ribonuclease residues observed to form a hydrogen bond to RI. In RNase 1, 13 residues form at least one hydrogen bond to RI, compared to 8 in RNase A.

Previous studies on RNase A and BS-RNase binding to RI focused on three structural regions, residues 38/39, residue 67, and residues in the (β4-β5 loop. FIGS. 2 and 3 emphasize the hydrogen bonding network and electron density of these regions for the hRI•RNase 1 complex. Arg39 of RNase 1 forms three hydrogen bonds with hRI that are absent with Arg39 in RNase A. Arg39 of RNase 1 makes a bidentate hydrogen bond with Glu401 and a main-chain hydrogen bond to Tyr434 of hRI. The hydrogen bond formed from Asn67 to RI shifts from Val405 (Leu409 in hRI) in pRI•RNase A to Tyr437 in hRI RNase 1. The β4-β5 loop forms hydrogen bonds involving Asn88, Gly89, and Arg91 (FIG. 2). Arg91 of RNase 1 forms two tight hydrogen bonds (< 3.0 Å) from the nitrogens in its guanidino group to Glu287 in hRI (FIG. 3).

In contrast, Lys91 in RNase A is directed away from Glu287 in pRI and no hydrogen bonds were observed (FIG. 2).[15] Based on the structural environment of the complementarity regions, two variants of RNase 1 were designed. One variant of RNase 1 (G38R/R39G/N67R/N88R RNase 1) mimics the most cytotoxic variant of RNase A (D38R/R39D/N67R/G88R RNase A), by swapping the amino acids in positions 38/39 and by incorporating bulky residues at positions 67 and 88. The other RNase 1 variant (R39D/N67D/N88A/G89D/R91D RNase 1) utilizes the same regions, but instead of steric bulk utilizes electrostatic repulsion to inhibit the binding of RI.

Ribonucleolytic Activity

The ability of a ribonuclease to cleave RNA in the presence of RI is closely correlated to its cytotoxicity in vitro. For a ribonuclease variant to achieve its full cytotoxic potential, a mutation that decreases RI binding must not detrimentally affect the native catalytic activity.[25] Consequently, variants of RNase 1 were assayed for their catalytic activity toward a tetranucleotide substrate. Values of $k_{cat}/K_M$ for RNase A, RNase 1, and their variants are given in Table 5. The $k_{cat}/K_M$ value for wild-type RNase 1 is 10-fold higher than the value previously reported. A similar increase in the catalytic activity was measured for RNase A when oligovinyl sulfonate, a potent inhibitor of ribonuclease, was removed from the reaction buffer.

TABLE 5

Biochemical parameters of RNase 1, RNase A, and their variants.

| Ribonuclease | Tin[a] (° C.) | $k_{cat}/K_M$[b] ($10^6\ M^{-1}s^{-1}$) | $K_d$[c] (nM) | ΔΔG[d] (kcal/mol) | ΔΔΔG[e] (kcal/mol) | $IC_{50}$[f] (μM) | Z |
|---|---|---|---|---|---|---|---|
| Wild-type RNase A | 64[g] | 52 ± 4[g] | $44 \times 10^{-6}$[h] | | | >25 | +4 |
| D38R/R39D/N67R/G88R RNase A | 56[g] | 38 ± 6[g] | 510 ± 30[g] | | | 0.15 ± 0.01 | +6 |

TABLE 5-continued

Biochemical parameters of RNase 1, RNase A, and their variants.

| Ribonuclease | Tin[a] (° C.) | $k_{cat}/K_M$[b] ($10^6 M^{-1}s^{-1}$) | $K_d$[c] (nM) | ΔΔG[d] (kcal/mol) | ΔΔΔG[e] (kcal/mol) | $IC_{50}$[f] (μM) | Z |
|---|---|---|---|---|---|---|---|
| Wild-type RNase 1 | 57 | 21 ± 2 | $20 \times 10^{-5}$[i] | | | >25 | +6 |
| G38R/R39G/N67R/N88R RNase 1 | 61 | 4.2 ± 0.4 | 0.032 ± 0.016 | 3.0 | | >25 | +8 |
| R39D/N67D/N88A/G89D/R91D RNase 1 | 58 | 6.3 ± 0.5 | $(1.7 \pm 0.5) \times 10^3$ | 9.5 | | 13.3 ± 1.7 | 0 |
| R39L/N67L/N88A/G89L/R91L RNase 1 | 65 | 30 ± 3 | 30 ± 1 | 7.1 | 2.4 | >25 | +4 |
| N67D/N88A/G89D/R91D RNase 1 | 51 | 16 ± 6 | 45 ± 15 | 7.3 | 2.2 | >25 | +2 |
| R39D/N88A/G89D/R91D RNase 1 | 57 | 10 ± 3 | 68 ± 8 | 7.6 | 1.9 | >25 | +1 |
| R39D/N67D/G89D/R91D RNase 1 | 54 | 3.3 ± 0.5 | $(1.0 \pm 0.1) \times 10^3$ | 9.1 | 0.4 | >25 | 0 |
| R39D/N67D/N88A/R91D RNase 1 | 51 | 10 ± 1 | 278 ± 50 | 8.4 | 1.1 | >25 | +1 |
| R39D/N67D/N88A/G89D RNase 1 | 57 | 5 ± 1 | 16 ± 3 | 6.7 | 2.8 | >25 | +2 |

[a]Values of $k_{cat}/K_M$ (±SE) were determined for catalysis of 6-FAM-dArU$(dA)_2$-6-TAMRA cleavage at 25° C. in 0.10 M MES-NaOH buffer (OVS-free), pH 6.0, containing 0.10 M NaCl (9).

[b]Values of $T_m$ (±2° C.) for RNase 1 and its variants were determined in PBS by UV spectroscopy.

[c]Values of $K_d$ (±SE) were determined for the complex with hR1 at 25° C. (10)

[d]Values of ΔΔG were calculated with the equation: $\Delta\Delta G = -RT\ln(K_d^{wild\text{-}type}/K_d^{variant})$.

[e]Values of $\Delta\Delta\Delta G = \Delta\Delta G^{R39D/N67D/N88A/G89D/R91D\ RNase\ 1} - \Delta\Delta G^{RNase\ 1\ variant}$.

[f]Values for $IC_{50}$ (±SE) are for incorporation of [methyl-$^3$H]thymidine into the DNA of K-562 cells treated with the ribonuclease. and were calculated with eq 1.

[g]From Rutkoski et al.

[h]From Lee et al.

[i]From Saxena et al.

The $k_{cat}/K_M$ values for all variants of RNase 1 are within 6-fold of the wild-type enzyme. Unlike RNase A, substitutions at residues 38/39, residue 67, and the residues in the β4-β5 loop of RNase 1 can detrimentally affect the catalytic activity. The influence of these residues is observed in the 5-fold and 3.3-fold decrease in activity of G38R/R39G/N67R/N88R RNase 1 and R39D/N67D/N88A/G89D/R91D RNase 1, respectively. An anomaly to this trend is R39L/N67L/N88A/G89L/R91L whose catalytic activity is unaffected by substitutions at these residues. The discrepancy could result from a compensating favorable hydrophobic interaction between the substituted leucines and the substrate nucleotide bases, although none of the positions mutated were previously proposed to be involved in substrate binding.

By reverting only one substitution in R39D/N67D/N88A/G89D/R91D RNase 1 to the wild-type amino acid (Table 5), the contribution of individual mutations to the $k_{cat}/K_M$ value can be deduced. For example in R39D/N67D/N88A/G89D/R91D RNase 1, an aspartate residue at position 39 decreases the activity 2.5-fold with respect to N67D/N88A/G89D/R91D RNase 1. Substitutions of N67D or G89D are responsible for a 1.6-fold decrease in the $k_{cat}/K_M$ value, where as mutations of R91D and N88A lead to a 1.3-fold and 1.9-fold increase in the $k_{cat}/K_M$ value, respectively. The contribution to the catalytic activity of each substitution in R39D/N67D/N88A/G89D/R91D RNase 1 seems to be additive as the total change in the $k_{cat}/K_M$ value for all five single substitutions (2.6-fold) approaches the 3.3-fold reduction in the $k_{cat}/K_M$ value for R39D/N67D/N88A/G89D/R91D RNase 1.

In regard to R4C/G38R/R39G/N67R/N88L/G89R/R91G/V118C RNase 1, it was found to retain nearly all of the enzymatic activity of the wild-type enzyme, having a $k_{cat}/K_M$ value of $(1.4 \pm 0.8) \times 10^6$ $M^{-1}s^{-1}$ under similar assay conditions.

Thermal Stability

The thermal stability of a ribonuclease is linked to its susceptibility to proteolysis and consequently its cytotoxicity. The $T_m$ values for all RNase 1 variants are shown in Table 5. The $T_m$ value of wild-type of RNase 1 is close to the previously reported value. In agreement with previous studies, incorporation of charged patches on the surface of RNase 1 does not reduce the $T_m$ value by more than 6° C. Neither arginine nor aspartate substitutions at residues 38/39, residue 67, or residues in the β4-β55 loop significantly disturb the conformational stability, as G38R/R39G/N67R/N88R RNase 1 and R39D/N67D/N88A/G89D/R91D RNase 1 have $T_m$ values comparable to wild-type RNase 1 (61 and 58° C., respectively.) The largest change in the conformational stability is observed with certain combinations of aspartate substitutions. For instance, N67D/N88A/G89D/R91D and R39D/N67D/N88A/R91D decrease the $T_m$ value by 6° C. and R39D/N67D/G89D/R91D by 3° C. Each of these RNase 1 variants has substitutions of both N67D and R91D, where as variants with only an N67D or R91D substitution have wild-type stability. Positions 67 and 91 are located on opposite sides of the RNase 1 active site, so an explanation for their synergistic contribution to thermal stability will require further study. Overall, all variants of RNase 1 are stable well above physiological temperature.

Evasion of Ribonuclease Inhibitor

RI binds multiple members of the RNase A superfamily with equilibrium dissociation constant values in the femtomolar range, forming one of the tightest noncovalent biological interactions. By mutating residues 38/39, 67, and 88 in RNase A (D38R/R39D/N67R/G88R RNase A), the equilibrium dissociation constant of the hRI•RNase A complex was increased by seven orders of magnitude (Table 5). The analogous variant in RNase 1 (G38R/R39G/N67R/N88R RNase 1) maintained near wild-type affinity (Table 5). However, substituting the arginine residues in G38R/R39G/N67R/N88R RNase 1 with multiple aspartate residues and one alanine residue reduces the affinity of RI for RNase 1 by nearly $10^7$-fold. The $K_d$ value for R39D/N67D/N88A/G89D/R91D RNase 1 (1.7 μM) is close to the highest measured for any RNase A variant (2.9 μM). When the aspartate substitutions in R39D/N67D/N88A/G89D/R91D RNase 1 are replaced with the isosteric amino acid, leucine (R39L/N67L/N88A/G89L/R91L RNase 1), the equilibrium dissociation constant increases 50-fold, Leucine substitution causes the disruption of 7 kcal/mol of RI-binding energy by the loss of electrostatic attraction and steric hindrance, but an additional 2.4 kcal/mol of binding energy is disturbed by the electrostatic repulsion of an aspartate residue at the same positions.

The influence of electrostatics on RI evasion is further expanded in Table 6, where the individual kinetic rate constants for the complex of hRI and two fluorescein-labeled RNase 1 variants are shown. The dissocation rate increases 1400-fold over wild-type RNase 1 upon substitutions of R39L/N67L/N88A/G89L/R91L in RNase 1, but remains nearly constant (2-fold increase) upon aspartate substitution (R39D/N67D/N88A/G89D/R91D RNase 1). The association rate is affected more proportionally by both leucine substitution (110-fold decrease) and by aspartate substitutions (25-fold decrease). The substantial change in the association rate with both leucine and aspartate demonstrates the two electrostatic forces that can lower the km value, loss of attractive forces (leucine substitution) and gain of repulsive forces (aspartate substitution). Overall, the nearly $10^7$-fold decrease in binding affinity of hRI for R39D/N67D/N88A/G89D/R91D RNase 1 contains equal contributions by the dissociation rate (3100-fold) and association rate (2700-fold). Yet, the additional 50-fold decrease in the $K_d$ value of R39D/N67D/N88A/G89D/R91D RNase 1 over R39L/N67L/N88A/G89L/R91L RNase 1 is driven by a decreased association rate.

TABLE 6

Contribution of the kinetic rate constants to overall R1 binding affinity

| Ribonuclease | $k_{off}(s^{-1})^a$ | $k_{on}\ (M^{-1}s^{-1})^b$ |
|---|---|---|
| wild-type RNase 1 | $6.8 \times 10^{-5c}$ | $3.4 \times 10^{8d}$ |
| R39D/N67D/N88A/G89D/R91D RNase 1 | $0.22 \pm 0.03\ (3.1 \times 10^3)$ | $1.2 \times 10^5\ (2.7 \times 10^3)$ |
| R39L/N67L/N88A/G89L/R91L RNase 1 | $0.092 \pm 0.003\ (1.4 \times 10^3)$ | $3.1 \times 10^6\ (1.1 \times 10^2)$ |

[a]Values for $k_{off}$ (±SE) were determined by following the release of a fluorescein-labeled RNase 1 variant from hRI over time and fitting the curves to eq 1. Values in parentheses represent the fold decrease from wild-type RNase 1.
[b]Values of $k_{on}$ were calculated using the equation, $K_d = k_{off}/k_{on}$. Numbers in parentheses represent the fold decrease from wild-type RNase 1.
[c]Value of $k_{off}$ was calculated using the equation, $K_d = k_{off}/k_{on}$. Where the $K_d$ value was from Boix et al. and the $k_{on}$ was for hRI/RNase A from Lee et al.
[d]Value of $k_{on}$ for hRI/RNase A from Lee et al.

The impact of individual mutations in R39D/N67D/N88A/G89D/R91D RNase 1 to its overall binding constant is elucidated by the reversion of each substitution in R39D/N67D/N88A/G89D/R91D RNase 1 to the wild-type amino acid. Residues with little impact on RI affinity will have small ΔΔΔG values in Table 5. Small ΔΔΔG values reflect a small change in the ΔΔG value when that one residue was reverted to the wild-type amino acid in R39D/N67D/N88A/G89D/R91D RNase 1. The ΔΔΔG values rank the energetic contributions of the mutations as N88A< G89D< N67D< R39D< R91D.

FIG. 4A plots the binding isotherm of each RNase 1 variant and illustrates the affinity of RNase 1 variants for hRI. Binding to hRI was determined by using a competition assay with fluorescently-labeled G88R RNase A (50 nM). The concentration of bound F*-A19C G88R RNase A was determined by following the decrease in fluorescein emission upon hRI binding. Data points are the mean (±SE) of at least three separate measurements. Variants in order of decreasing hRI-affinity: R39D/N67D/N88A/G89D (■); N67D/N88A/G89D/R91D (Δ); R39D/N88A/G89D/R91D (●); R39D/N67D/N88A/R91D (○); R39D/N67D/G89D/R91D (▼); R39D/N67D/N88A/G89D/R91D (⎵). The results of this experiment illustrates this same trend as indicated above for the individual mutations. An aspartate at position 91 contributed 2.8 kcal/mol of energy to evasion, 0.6 kcal/mol more than any other residue. Conversely, aspartates at both positions 88 and 89 contributed only 1.5 kcal/mol, which is lower than the energetic contribution of any other single substitution, showing that different residues play a more important role in hRI•RNase 1 complex formation as compared to pRI•RNase A.

In regard to R4C/G38R/R39G/N67R/N88L/G89R/R91G/V118C RNase 1, it was found that the value of $K_d$ for the complex of hRI and R4C/G38R/R39G/N67R/N88L/G89R/R91G/V118C RNase 1 is $(5.5\pm1.6)\times10^{-8}$ M. The value of the equilibrium dissociation constant, $K_d$, for the complex of hRI with wild-type RNase 1 is not known, but likely to be near the value of $10^{-14}$ M for the complex of porcine RI with bovine pancreatic ribonuclease (RNase A).

Charge and Cytotoxicity

The cytotoxicity of a ribonuclease is governed by all of the preceding ribonuclease attributes and the molecular charge of a ribonuclease. The interplay between the molecular charge and the cytotoxicity of a ribonuclease is seen with the results in FIG. 4B and Table 5.

In particular. FIG. 4B shows the effect of ribonucleases on the proliferation of K-562 cells. The incorporation of [methyl-$^3$H]thymidine into cellular DNA was used to monitor the proliferation of K-562 cells in the presence of ribonucleases. Data points are the mean (±SE) of at least three separate experiments carried out in triplicate. Variants in order of increasing cytotoxicity: D38R/R39D/N67R/G88R RNase A (Λ); G88R RNase A (○); R39D/N67D/N88A/G89D/R91D RNase 1 (▲); R39L/N67L/N88A/G89L/R91L RNase 1 (●); N67D/N88A/G89D/R91D RNase 1 (♦); G38R/R39G/N67R/N88R RNase 1 (■); and wild-type RNase 1 (⎵). All other variants of RNase 1 from Table 5 had curves comparable to that of G38R/R39G/N67R/N88R RNase 1 and, for clarity, are not shown.

Figure 4:
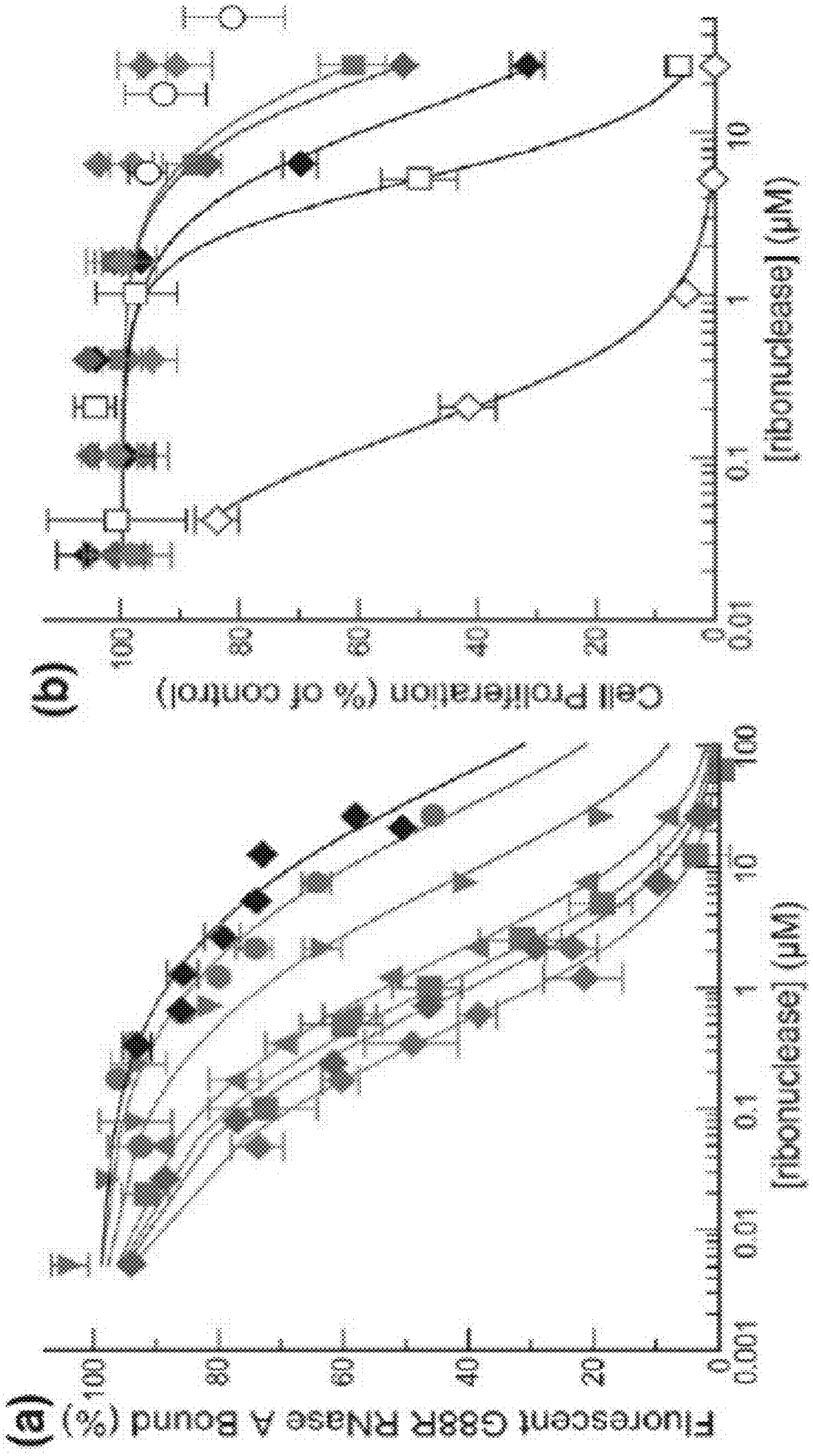
FIGS. 4A-B show hRI-Affinity and cytotoxicity of RNase 1 and its variants. Legend for FIG. 4A is as follows: R39D/N67D/N88A/G89D (■); N67D/N88A/G89D/R91D (Δ); R39D/N88A/G89D/R91D (●); R39D/N67D/N88A/R91D (○); R39D/N67D/G89D/R91D (▼); R39D/N67D/N88A/G89D/R91D (□). Legend for FIG. 4B is as follows; D38R/R39D/N67R/G88R RNase A (Λ); G88R RNase A (○); R39D/N67D/N88A/G89D/R91D RNase 1 (▲); R39L/N67L/N88A/G89L/R91L RNase 1 (●); N67D/N88A/G89D/R91D RNase 1 (♦); G38R/R39G/N67R/N88R RNase 1 (■); and wild-type RNase 1 (□).

FIG. 4B illustrates that D38R/R39D/N67R/G88R RNase A has the same conformational stability, a 6-fold higher $k_{cat}/K_M$ value, and a 3-fold lower $K_d$ value than R39D/N67D/N88A/G89D/R91D RNase 1, but their $IC_{50}$ values differ by a disproportionately large 87-fold. R39D/N67D/N88A/G89D/R91D RNase 1 has an $IC_{50}$ of only 13.3 μM, making it more toxic than wild-type RNase 1 (FIG. 4), but 2-fold less toxic than G88R RNase A. The only biochemical characteristic that differs significantly between D38R/R39D/N67R/G88R RNase A (+6) and R39D/N67D/N88A/G89D/R91D RNase 1 (0) is the net charge.

The $IC_{50}$ values of all the other variants of RNase 1 from Table 5 fall outside the measurable range of the assay. R39L/N67L/N88A/G89L/R91L RNase 1 and N67D/N88A/G89D/R91D RNase 1, however, have killed approximately 60% of the K-562 cells at 25 μM (FIG. 4), putting their $IC_{50}$ values just slightly above 25 μM. The lack of cytotoxicity for most RNase 1 variants other than R39D/N67D/N88A/G89D/R91D RNase 1 can be explained by an increased affinity for RI or loss in thermal stability when compared to R39D/N67D/N88A/G89D/R91D RNase 1. The outlier to this trend is N67D/N88A/G89D/R91D RNase 1, whose $K_d$ value is 57-fold lower than R39D/N67D/N88A/G89D/R91D but whose $IC_{50}$ value is estimated to be only 2-fold higher. Part of the anomalous cytotoxicity of N67D/N88A/G89D/R91D RNase 1 can be attributed to a 3-fold increase in the catalytic activity over R39D/N67D/N88A/G89D/R91D RNase 1, but the increased activity does not completely explain the disproportionately high cytotoxicity of N67D/N88A/G89D/R91D RNase 1.

Furthermore, in assays we conducted with human chronic myelogenous leukemia cell line K-562, wild-type RNase 1 has an $IC_{50}$ value of >50 μM. In contrast, R4C/G38R/R39G/N67R/N88L/G89R/R91G/V118C RNase 1 exhibits significant cytotoxic activity, having an $IC_{50}$ value of 15 μM.

Taken together, the preceding examples demonstrate the creation of cytotoxic ribonuclease variants by exploiting the electrostatic interaction between hRI and RNase 1, such that the variants evade RI binding, with little compromise to catalytic efficacy. It is to be understood that the present invention is not limited to the particular embodiments disclosed in this application, but embraces all such modified forms thereof that come within the scope of the following claims.

Human Ribonuclease as a Chemotherapeutic

Ribonucleases show great promise as cancer chemotherapeutics.[12] ONC, a homologue of RNase 1 from the northern leopard frog, is currently in phase III clinical trials for the treatment of malignant mesothelioma. However, therapeutics of RNase 1 have multiple advantages over ONC, including enhanced catalytic activity,[13] decreased renal toxicity, and decreased immunogenicity. To develop therapeutics of ribonucleases that are not naturally cytotoxic, requires the careful consideration of multiple biochemical attributes including thermal stability, catalytic activity, charge, and especially RI evasion.

Variants of RNase 1 with lower affinity for hRI have been difficult to engineer using natural amino acid substitutions. However, using the structural and electrostatic information obtained from the crystal structure of the hRI•RNase 1 complex, we have removed this hindrance to cytotoxicity by designing a variant of RNase 1 with an affinity for RI in the micromolar range. R39D/N67D/N88A/G89D/R91D RNase 1 has near native catalytic activity and conformational stability, but its cytotoxicity is hindered by lowered positive charge (Table 5 and FIG. 4). Ribonuclease variants with lower net charge have increased $IC_{50}$ values when compared to ribonucleases with similar activity, stability, and RI affinity.[13] However, the charge on a ribonuclease can be increased by adding additional positive charge to the termini, which increased the toxicity of RNase A. By greatly decreasing the inhibition of RNase 1 by hRI, we have eliminated a barrier to ribonuclease cytotoxicity and opened the door to human ribonuclease-based therapies.

The tight inhibitory complexes between ribonucleases and RI provide a good model system for studying the influence of electrostatics on the association of protein-protein complexes. To this end, we have looked at RNase 1, the structural and sequence homologue of RNase A, whose interaction with hRI has been difficult to predict. By determining the X-ray crystal structure of RNase 1 in complex with hRI and studying key electrostatic hotspots, we were able to create variants of RNase 1 with micromolar affinity for hRI. Substitution of key charged residues created the greatest change in binding affinity and suggests a new class of anchor residues for protein-protein interactions, electrostatic anchor residues. Mutation of electrostatic anchors like Arg39 or Arg91 changes the affinity by influencing the association rate of the complex. We reduced the affinity of hRI for RNase 1 by $10^7$-fold by exploiting the electrostatic anchors on RNase 1. Accordingly, the variants of RNase 1 that evade RI-binding represent a large step in the development of chemotherapeutics using human ribonucleases.

All publications and patents mentioned in the above specification are herein incorporated by reference as if expressly set forth herein. Although the foregoing invention has been described in some detail by way of illustration and example for purposes of clarity of understanding, it is understood that certain adaptations of the invention are a matter of routine optimization for those skilled in the art, and can be implemented without departing from the spirit of the invention, or the scope of the appended claims.

RELATED PUBLICATIONS

1. Shaul, Y. & Schreiber, G. Exploring the charge space of protein-protein association: a proteomic study. Proteins 60, 341-352 (2005).
2. Rutkoski, T. J., Kurten, E. L., Mitchell, J. C. & Raines, R. T. Disruption of shapecomplentarity markers to create cytotoxic variants of ribonuclease A. J. Mol. Biol. 354, 41-54 (2005).
3. Mitchell, J. C., Kerr. R. & Ten Eyck, L. F. Rapid atomic density methods for molecular shape characterization. J. Mol. Graph. Model. 19, 325-330 (2001).
4. Kobe, B. & Deisenhofer, J. A structural basis of the interactions between leucine-rich repeats and protein ligands. Nature 374, 183-186 (1995).
5. Lee, J. E. & Raines, R. T. Cytotoxicity of Bovine Seminal Ribonuclease. Monomer versus Dimer. Biochemistry 44, 15760-15767 (2005).
6. Leland, P. A., Schultz, L. W., Kim, B.-M. & Raines, R. T. Ribonuclease A variants with potent cytotoxic activity. Proc. Natl. Acad. Sci. U.S.A. 98, 10407-10412 (1998).
7. Leland, P. A., Staniszewski, K. E., Kim, B.-M. & Raines, R. T. Endowing human pancreatic ribonuclease with toxicity for cancer cells. J. Biol. Chem. 276, 43095-43102 (2001).
8 Gaur. D., Swaminathan, S. & Batra, J. K. Interaction of human pancreatic ribonuclease with human ribonuclease inhibitor. J. Biol. Chem. 276, 24978-24984 (2001).
9. Bosch, M. et al. A nuclear localization sequence endows human pancreatic ribonuclease with cytotoxic activity. Biochemistry 43, 2167-2177 (2004).
10. Rajamani, D., Thiel, S., Vajda, S. & Camacho, C. J. Anchor residues in protein-protein interactions. Proc. Natl. Acad. Sci. U.S.A. 101, 11287-11292 (2004).
11. Pous, J. et al. Three-dimensional structure of human RNase 1 delta N7 at 1.9 Å resolution. Acta Crystallogr. D Biol. Crystallogr. 57.498-505 (2001).
12. Pous, J. et al. Three-dimensional structure of a human pancreatic ribonuclease variant, a step forward in the design of cytotoxic ribonucleases. J. Mol. Biol. 303, 49-60 (2000).
13. Boix. E., Wu, Y., Vasandani, V. M., Saxena, S. K., Ardelt, W., Ladner, J. & Youle, R. J. (1996). J. Mol. Biol. 257, 992-1007.

We claim:

1. A method for inhibiting the proliferation of cancer cells, comprising delivering to the cells an effective amount of an engineered human Ribonuclease (RNase 1) polypeptide, said polypeptide comprising SEQ ID NO:2 except for one or more amino acid substitutions in the region of amino acid residues 85 to 94 and one or more amino acid substitutions selected from the group consisting of substitutions at position 4, 38, 39, 67, and 118 of SEQ ID NO:2.

2. The method of claim 1, wherein said amino acid substitutions at positions 4, 38, 39, 67 and 118 are R4C, G38R, R39G, N67R, and V118C.

3. The method of claim 1, wherein said amino acid substitution in the region of amino acid residues 85 to 94 is N88L.

4. The method of claim 1, wherein said amino acid substitution in the region of amino acid residues 85 to 94 is G89R.

5. The method of claim 1, wherein said amino acid substitution in the region of amino acid residues 85 to 94 is R91G.

6. A method for inhibiting the proliferation of cancer cells, comprising delivering to the cells an effective amount of an engineered human Ribonuclease (RNase 1) polypeptide, said polypeptide comprising SEQ ID NO:2 except for one or more amino acid substitutions in the region of amino acid residues 85 to 94 and one or more of the following amino acid substitutions: R4C, G38R, R39G, N67R, or V118C relative to SEQ ID NO:2.

7. A method for inhibiting the proliferation of cancer cells, comprising delivering to the cells an effective amount of an engineered human Ribonuclease (RNase 1) polypeptide, said polypeptide comprising SEQ ID NO:2 except for one or more amino acid substitutions in the region of amino acid residues 85 to 94 and one or more amino acid substitutions at position 4, 38, 39, 67 or 118 of SEQ ID NO:2.

8. The method of claim 7, wherein said amino acid substitutions at position 4, 38, 39, 67 or 118 are R4C, G38R, R39G, N67R, and V118C.

9. The method of claim 7, wherein said amino acid substitution in the region amino acid residues 85 to 94 is N88L.

10. The method of claim 7, wherein said amino acid substitution in the region of amino acid residues 85 to 94 is G89R.

11. The method of claim 7, wherein said amino acid substitution in the region of amino acid residues 85 to 94 is R91G.

12. The method of claim 1, wherein the amino acid substitutions are R4C, G38R, R39G, N67R, N88L, G89R, R91G, and V118C.

13. The method of claim 6, wherein the amino acid substitutions are R4C, G38R, R39G, N67R, N88L, G89R, R91G, and V118C.

14. The method of claim 7, wherein the amino acid substitutions are R4C, G38R, R39G, N67R, N88L, G89R, R910, and V118C.

15. A method for inhibiting the proliferation of cancer cells, comprising delivering to the cells an effective amount of an engineered human Ribonuclease (RNase 1) polypeptide, said polypeptide comprising SEQ ID NO:2 except for the following amino acid substitutions: R4C, G38R, R39G, N67R, N88L, G89R, R91G, and V118C relative to SEQ ID NO:2.

16. The method of claim 1, 6 or 7, wherein the engineered RNase 1 retains ribonucleolytic activity relative to SEQ ID NO:2.

17. The method of claim 1, 6 or 7, wherein the engineered RNase 1 exhibits enhanced cytotoxic activity relative to SEQ ID NO: 2.

18. The method of claim 1, 6 or 7, wherein the engineered RNase 1 exhibits a lower binding affinity for hRI than SEQ ID NO:2.

19. The method of claim 1, 6 or 7, wherein the engineered RNase 1 retains ribonucleolytic activity, exhibits enhanced cytotoxic activity relative to SEQ ID NO: 2, and has a lower binding affinity for hRI than SEQ ID NO:2.

20. The method of claim 1, 6 or 7, wherein the one or more amino acid substitutions in SEQ ID NO:2 electrostatically repel and/or sterically hinder binding of human Ribonuclease Inhibitor (hRI) to the engineered RNase 1.

* * * * *

UNITED STATES PATENT AND TRADEMARK OFFICE

CERTIFICATE OF CORRECTION

PATENT NO. : 8,048,425 B2
APPLICATION NO. : 12/497038
DATED : November 1, 2011
INVENTOR(S) : Raines et al.

It is certified that error appears in the above-identified patent and that said Letters Patent is hereby corrected as shown below:

Please replace Claim 14 as follows:

Column 30, Claim 14:
-- The method of claim 7, wherein the amino acid substitutions are R4C, G38R, R39G, N67R, N88L, G89R, R91G, and V118C. --

Signed and Sealed this
Seventeenth Day of January, 2012

David J. Kappos
*Director of the United States Patent and Trademark Office*

UNITED STATES PATENT AND TRADEMARK OFFICE

CERTIFICATE OF CORRECTION

PATENT NO. : 8,048,425 B2
APPLICATION NO. : 12/497038
DATED : November 1, 2011
INVENTOR(S) : Raines et al.

It is certified that error appears in the above-identified patent and that said Letters Patent is hereby corrected as shown below:

Please replace Column 30, lines 35-37, Claim 14 as follows:

-- The method of claim 7, wherein the amino acid substitutions are R4C, G38R, R39G, N67R, N88L, G89R, R91G, and V118C. --

This certificate supersedes the Certificate of Correction issued January 17, 2012.

Signed and Sealed this
Fourteenth Day of February, 2012

David J. Kappos
*Director of the United States Patent and Trademark Office*

SEQUENCE LISTING

```
<160> NUMBER OF SEQ ID NOS: 4

<210> SEQ ID NO 1
<211> LENGTH: 123
<212> TYPE: PRT
<213> ORGANISM: Bos taurus
```

-continued

<400> SEQUENCE: 1

Lys Glu Thr Ala Ala Ala Lys Phe Glu Arg Gln His Met Asp Ser Ser
1 5 10 15

Thr Ser Ala Ala Ser Ser Ser Asn Tyr Cys Asn Gln Met Met Lys Ser
20 25 30

Arg Asn Leu Thr Lys Asp Arg Cys Lys Pro Val Asn Thr Phe Val His
35 40 45

Glu Ser Leu Ala Asp Val Gln Ala Val Cys Ser Gln Lys Asn Val Ala
50 55 60

Cys Lys Asn Gly Gln Thr Asn Cys Tyr Gln Ser Tyr Ser Thr Met Ser
65 70 75 80

Ile Thr Asp Cys Arg Glu Thr Gly Ser Ser Lys Pro Asn Cys Ala Tyr
85 90 95

Lys Thr Thr Gln Ala Asn Lys His Ile Ile Val Ala Cys Glu Gly Asn
100 105 110

Pro Tyr Val Pro Val His Phe Asp Ala Ser Val
115 120

<210> SEQ ID NO 2
<211> LENGTH: 128
<212> TYPE: PRT
<213> ORGANISM: Homo sapiens

<400> SEQUENCE: 2

Lys Glu Ser Arg Ala Lys Lys Phe Gln Arg Gln His Met Asp Ser Asp
1 5 10 15

Ser Ser Pro Ser Ser Ser Ser Thr Tyr Cys Asn Gln Met Met Arg Arg
20 25 30

Arg Asn Met Thr Gln Gly Arg Cys Lys Pro Val Asn Thr Phe Val His
35 40 45

Glu Pro Leu Val Asp Val Gln Asn Val Cys Phe Gln Glu Lys Val Thr
50 55 60

Cys Lys Asn Gly Gln Gly Asn Cys Tyr Lys Ser Asn Ser Ser Met His
65 70 75 80

Ile Thr Asp Cys Arg Leu Thr Asn Gly Ser Arg Tyr Pro Asn Cys Ala
85 90 95

Tyr Arg Thr Ser Pro Lys Glu Arg His Ile Ile Val Ala Cys Glu Gly
100 105 110

Ser Pro Tyr Val Pro Val His Phe Asp Ala Ser Val Glu Asp Ser Thr
115 120 125

<210> SEQ ID NO 3
<211> LENGTH: 127
<212> TYPE: PRT
<213> ORGANISM: Homo sapiens

<400> SEQUENCE: 3

Lys Glu Ser Arg Ala Lys Lys Phe Gln Arg Gln His Met Asp Ser Asp
1 5 10 15

Ser Ser Pro Ser Ser Ser Ser Thr Tyr Cys Asn Gln Met Met Arg Arg
20 25 30

Arg Asn Met Thr Gln Gly Arg Cys Lys Pro Val Asn Thr Phe Val His
35 40 45

Glu Pro Leu Val Asp Val Gln Asn Val Cys Phe Gln Glu Lys Val Thr
50 55 60

Cys Lys Asn Gly Gln Gly Asn Cys Tyr Lys Ser Asn Ser Ser Met His

-continued 65 70 75 80

Ile Thr Asp Cys Arg Leu Thr Asn Gly Ser Arg Pro Asn Cys Ala Tyr
85 90 95

Arg Thr Ser Pro Lys Glu Arg His Ile Ile Val Ala Cys Glu Gly Ser
100 105 110

Pro Tyr Val Pro Val His Phe Asp Ala Ser Val Glu Asp Ser Thr
115 120 125

<210> SEQ ID NO 4
<211> LENGTH: 461
<212> TYPE: PRT
<213> ORGANISM: Homo sapiens

<400> SEQUENCE: 4

Met Ser Leu Asp Ile Gln Ser Leu Asp Ile Gln Cys Glu Glu Leu Ser
1 5 10 15

Asp Ala Arg Trp Ala Glu Leu Leu Pro Leu Leu Gln Gln Cys Gln Val
20 25 30

Val Arg Leu Asp Asp Cys Gly Leu Thr Glu Ala Arg Cys Lys Asp Ile
35 40 45

Ser Ser Ala Leu Arg Val Asn Pro Ala Leu Ala Glu Leu Asn Leu Arg
50 55 60

Ser Asn Glu Leu Gly Asp Val Gly Val His Cys Val Leu Gln Gly Leu
65 70 75 80

Gln Thr Pro Ser Cys Lys Ile Gln Lys Leu Ser Leu Gln Asn Cys Cys
85 90 95

Leu Thr Gly Ala Gly Cys Gly Val Leu Ser Ser Thr Leu Arg Thr Leu
100 105 110

Pro Thr Leu Gln Glu Leu His Leu Ser Asp Asn Leu Leu Gly Asp Ala
115 120 125

Gly Leu Gln Leu Leu Cys Glu Gly Leu Leu Asp Pro Gln Cys Arg Leu
130 135 140

Glu Lys Leu Gln Leu Glu Tyr Cys Ser Leu Ser Ala Ala Ser Cys Glu
145 150 155 160

Pro Leu Ala Ser Val Leu Arg Ala Lys Pro Asp Phe Lys Glu Leu Thr
165 170 175

Val Ser Asn Asn Asp Ile Asn Glu Ala Gly Val Arg Val Leu Cys Gln
180 185 190

Gly Leu Lys Asp Ser Pro Cys Gln Leu Glu Ala Leu Lys Leu Glu Ser
195 200 205

Cys Gly Val Thr Ser Asp Asn Cys Arg Asp Leu Cys Gly Ile Val Ala
210 215 220

Ser Lys Ala Ser Leu Arg Glu Leu Ala Leu Gly Ser Asn Lys Leu Gly
225 230 235 240

Asp Val Gly Met Ala Glu Leu Cys Pro Gly Leu Leu His Pro Ser Ser
245 250 255

Arg Leu Arg Thr Leu Trp Ile Trp Glu Cys Gly Ile Thr Ala Lys Gly
260 265 270

Cys Gly Asp Leu Cys Arg Val Leu Arg Ala Lys Glu Ser Leu Lys Glu
275 280 285

Leu Ser Leu Ala Gly Asn Glu Leu Gly Asp Glu Gly Ala Arg Leu Leu
290 295 300

Cys Glu Thr Leu Leu Glu Pro Gly Cys Gln Leu Glu Ser Leu Trp Val
305 310 315 320

Lys Ser Cys Ser Phe Thr Ala Ala Cys Cys Ser His Phe Ser Ser Val

-continued

```
                325                 330                 335

Leu Ala Gln Asn Arg Phe Leu Leu Glu Leu Gln Ile Ser Asn Asn Arg
            340                 345                 350

Leu Glu Asp Ala Gly Val Arg Glu Leu Cys Gln Gly Leu Gly Gln Pro
        355                 360                 365

Gly Ser Val Leu Arg Val Leu Trp Leu Ala Asp Cys Asp Val Ser Asp
    370                 375                 380

Ser Ser Cys Ser Ser Leu Ala Ala Thr Leu Leu Ala Asn His Ser Leu
385                 390                 395                 400

Arg Glu Leu Asp Leu Ser Asn Asn Cys Leu Gly Asp Ala Gly Ile Leu
                405                 410                 415

Gln Leu Val Glu Ser Val Arg Gln Pro Gly Cys Leu Leu Glu Gln Leu
            420                 425                 430

Val Leu Tyr Asp Ile Tyr Trp Ser Glu Glu Met Glu Asp Arg Leu Gln
        435                 440                 445

Ala Leu Glu Lys Asp Lys Pro Ser Leu Arg Val Ile Ser
    450                 455                 460
```